(12) United States Patent
Takaoka et al.

(10) Patent No.: US 10,065,140 B2
(45) Date of Patent: Sep. 4, 2018

(54) ABNORMALITY DIAGNOSIS APPARATUS FOR PARTICULATE FILTER

(71) Applicant: TOYOTA JIDOSHA KABUSHIKI KAISHA, Toyota-shi, Aichi-ken (JP)

(72) Inventors: Kazuya Takaoka, Gotemba (JP); Toru Kidokoro, Hadano (JP)

(73) Assignee: Toyota Jidosha Kabushiki Kaisha, Toyota-shi, Aichi-ken (JP)

( * ) Notice: Subject to any disclaimer, the term of this patent is extended or adjusted under 35 U.S.C. 154(b) by 203 days.

(21) Appl. No.: 15/083,472

(22) Filed: Mar. 29, 2016

(65) Prior Publication Data
US 2016/0288037 A1    Oct. 6, 2016

(30) Foreign Application Priority Data
Apr. 2, 2015    (JP) .................. 2015-076106

(51) Int. Cl.
| | |
|---|---|
| *B01D 53/22* | (2006.01) |
| *B01D 59/12* | (2006.01) |
| *B01D 46/00* | (2006.01) |
| *F01N 11/00* | (2006.01) |
| *G01N 27/416* | (2006.01) |
| *F01N 3/021* | (2006.01) |

(Continued)

(52) U.S. Cl.
CPC ..... *B01D 46/0095* (2013.01); *B01D 46/0057* (2013.01); *B01D 46/0086* (2013.01); *F01N 11/00* (2013.01); *G01N 27/416* (2013.01); *F01N 3/021* (2013.01); *F01N 3/023* (2013.01); *F01N 13/008* (2013.01); *F01N 2550/04* (2013.01); *F01N 2560/05* (2013.01); *F01N 2900/1606* (2013.01); *Y02T 10/47* (2013.01)

(58) Field of Classification Search
None
See application file for complete search history.

(56) References Cited

U.S. PATENT DOCUMENTS

| | | | |
|---|---|---|---|
| 8,783,097 B2 * | 7/2014 | Lim ................. | F01N 11/007 |
| | | | 73/114.71 |
| 2012/0144813 A1 | 6/2012 | Yahata et al. | |

(Continued)

FOREIGN PATENT DOCUMENTS

| | | |
|---|---|---|
| JP | 2011-179467 | 9/2011 |
| JP | 2012-77716 | 4/2012 |
| JP | 2012-122399 | 6/2012 |

*Primary Examiner* — Amber Rose Orlando
(74) *Attorney, Agent, or Firm* — Finnegan, Henderson, Farabow, Garrett & Dunner LLP

(57) ABSTRACT

Embodiments of the present disclosure improve the accuracy of abnormality diagnosis of a particulate filter using the output value of a PM sensor provided downstream of the particulate filter in an exhaust passage. A configuration of the invention compares a change rate of an output value of the PM sensor prior to execution of a filter diagnosis process of diagnosing an abnormality of the filter based on the output value of the PM sensor, with a reference value and determines whether a filter abnormality process is to be performed. A higher value is set to the reference value, which is to be compared with the change rate of the output value of the PM sensor, in the case where the deposition amount of PM between electrodes of the PM sensor is expected to be large, compared with the case where the deposition amount of PM is expected to be small.

6 Claims, 11 Drawing Sheets

(51) Int. Cl.
    *F01N 3/023*     (2006.01)
    *F01N 13/00*     (2010.01)

(56) References Cited

U.S. PATENT DOCUMENTS

| | | | | |
|---|---|---|---|---|
| 2012/0260636 | A1* | 10/2012 | Hashida | F01N 11/00 60/276 |
| 2015/0132187 | A1* | 5/2015 | Takaoka | F01N 3/2066 422/111 |
| 2015/0211405 | A1* | 7/2015 | Yoshidome | F01N 11/00 73/114.69 |
| 2015/0211429 | A1* | 7/2015 | Hocken | F02D 41/029 324/601 |

* cited by examiner

ABNORMALITY DIAGNOSIS APPARATUS FOR PARTICULATE FILTER This patent application claims the benefit of Japanese Patent Application No. 2015-076106, filed on Apr. 2, 2015, which is hereby incorporated by reference herein in its entirety.

BACKGROUND

Technical Field

The present disclosure relates to an abnormality diagnosis apparatus for a particulate filter that is provided in an exhaust passage of an internal combustion engine to trap PM (particulate matter) included in the exhaust gas.

Description of Background Art

There is a known technique to provide a particulate filter (hereinafter may be simply referred to as "filter") that is configured to trap PM included in the exhaust gas, in an exhaust passage of an internal combustion engine. A failure such as erosion or breakage may occur in the filter. The occurrence of such a failure increases the amount of PM that is not trapped by the filter but flows out of the filter. The occurrence of such a failure in the filter or the occurrence of an abnormality of the filter, for example, detachment of the filter from the exhaust passage, leads to an increase in PM released to the atmosphere. A proposed technique accordingly provides a PM sensor downstream of the filter in the exhaust passage and diagnoses an abnormality of the filter based on the output value of the PM sensor. A known configuration of the PM sensor used for abnormality diagnosis of the filter has a pair of electrodes as a sensor element and outputs a signal corresponding to the amount of PM depositing between the electrodes.

A technique disclosed in Patent Literature 1 compares an output value of a PM sensor provided downstream of a filter in an exhaust passage with an estimated value of a deposition amount of PM in the PM sensor to determine the presence or the absence of a failure in the filter. The technique described in Patent Literature 1 estimates a flow-out amount of PM from the filter on the assumption that the filter is in a predetermined state, and calculates an estimated value of the deposition amount of PM in the PM sensor based on the integrated value of the estimated flow-out amount of PM. The state of the filter may be detected by comparing the estimated value of the deposition amount of PM with the actual output value of the PM sensor.

A technique disclosed in Patent Literature 2 diagnoses a failure of a filter, based on the time when power supply is started by deposition of PM between electrodes of a PM sensor provided downstream of the filter in an exhaust passage. The technique described in Patent Literature 2 determines that a failure occurs in the filter in the case where the time when power supply is started between the electrodes of the PM sensor is earlier than a power supply start time on the assumption that a failure occurs in the filter.

Patent Literature 3 discloses a technique regarding detection of an abnormality of a PM sensor. The technique described in Patent Literature 3 burns out and removes PM depositing between electrodes of the PM sensor by heating with a heater. An abnormality of the PM sensor is detected, based on a change in resistance value between the electrodes relative to a burning removal time.

PATENT LITERATURE

Patent Literature 1: Japanese Patent Application Laid-Open No. 2011-179467A

Patent Literature 2: Japanese Patent Application Laid-Open No. 2012-122399A

Patent Literature 3: Japanese Patent Application Laid-Open No. 2012-077716A

SUMMARY

Technical Problem

As described above, the occurrence of a failure in the filter increases the flow-out amount of PM from the filter. This leads to an increase in amount of PM trapped between the electrodes of the PM sensor that is provided downstream of the filter in the exhaust passage. This provides the larger deposition amount of PM between the electrodes of the PM sensor, compared with the deposition amount of PM in the normal state of the filter. The same applies to the case where the filter is detached from the exhaust passage. Abnormality diagnosis of the filter can thus be performed, based on the output value of the PM sensor in a predetermined time period.

There is a likelihood that conductive materials other than PM as the original detection object (hereinafter referred to as extraneous substances) are trapped between the electrodes of the PM sensor. Even in the normal state of the filter, such extraneous substances may be trapped between the electrodes of the PM sensor. Trapping the extraneous substances between the electrodes of the PM sensor also varies the output value of the PM sensor. In the case of abnormality diagnosis of the filter based on the output value of the PM sensor in the state that extraneous substances are trapped between the electrodes of the PM sensor, there is a likelihood of wrong diagnosis to diagnose that the filter is abnormal, despite that the filter is actually normal.

Embodiments of the present disclosure improve the accuracy of abnormality diagnosis of a filter using the output value of a PM sensor provided downstream of the filter in an exhaust passage.

A configuration of the present disclosure compares a change rate of an output value of the PM sensor prior to execution of a filter diagnosis process of diagnosing an abnormality of the filter based on the output value of the PM sensor, with a reference value and determines whether a filter abnormality process is to be performed. A higher value is set to the reference value, which is to be compared with the change rate of the output value of the PM sensor, in the case where the deposition amount of PM between electrodes of the PM sensor is expected to be large, compared with the case where the deposition amount of PM is expected to be small.

More specifically, according to one aspect of the present disclosure, there is provided an abnormality diagnosis apparatus for a particulate filter that is provided in an exhaust passage of an internal combustion engine to trap PM included in exhaust gas. The abnormality diagnosis apparatus comprises: a PM sensor that is provided downstream of the particulate filter in the exhaust passage and is configured to have a pair of electrodes as a sensor element and output a signal corresponding to a deposition amount of PM between the electrodes when electrical continuity is established between the electrodes by deposition of PM between the electrodes, the PM sensor being configured such that a larger deposition amount of PM between the electrodes provides a higher variation in output value of the PM sensor relative to an increase in deposition amount of PM between the electrodes; a controller comprising at least one processor configured to perform a sensor recovery process of removing PM depositing between the electrodes of the PM sensor, and to perform a filter diagnosis process of diagnosing an abnormality of the particulate filter based on an output value of the PM sensor at a time when a predetermined determination time period has elapsed since a predetermined PM deposition restart time, which is a time when deposition of PM between the electrodes of the PM sensor is restarted after completion of the sensor recovery process; a monitor unit that is configured to continuously monitor an output signal of the PM sensor after the PM deposition restart time, wherein the controller determines that the filter diagnosis process is not to be performed when a sensor output change rate becomes higher than a predetermined determination change rate before elapse of the determination time period since the PM deposition restart time, wherein the sensor output change rate is a variation in output value of the PM sensor monitored by the monitor unit per unit increase in reference deposition amount of PM, wherein the reference deposition amount of PM is an estimated value of the deposition amount of PM between the electrodes of the PM sensor on the assumption that the particulate filter is in a predetermined reference state, or a variation in output value of the PM sensor monitored by the monitor unit per unit time, wherein the reference deposition amount of PM is an estimated value of the deposition amount of PM between the electrodes of the PM sensor on the assumption that the particulate filter is in a predetermined reference state; and the controller sets a higher value to the determination change rate, which is to be compared with the sensor output change rate, in a case where the deposition amount of PM between the electrodes of the PM sensor is expected to be large at a corresponding time to the sensor output change rate, compared with a case where the deposition amount of PM is expected to be small at a corresponding time to the sensor output change rate.

In the PM sensor of the present disclosure, when the amount of PM depositing between the electrodes as the sensor element becomes equal to or larger than a predetermined amount, electrical continuity is established between the electrodes by deposition of PM. The deposition amount of PM between the electrodes when electrical continuity is established between the electrodes of the PM sensor by deposition of PM is referred to as "effective deposition amount of PM". When the deposition amount of PM between the electrodes becomes equal to or larger than the effective deposition amount of PM, the PM sensor generates an output value corresponding to the deposition amount of PM between the electrodes. In the PM sensor configured to generate an output value that reflects the value of electric current flowing between the electrodes, the output value of the PM sensor increases with an increase in deposition amount of PM between the electrodes. In the PM sensor configured to generate an output value that reflects the resistance value between the electrodes, on the other hand, the output value of the PM sensor decreases with an increase in deposition amount of PM between the electrodes. The PM sensor of the present disclosure may have either of these output characteristics, as long as the PM sensor is configured to output a signal corresponding to the deposition amount of PM between the electrodes. The larger deposition amount of PM between the electrodes provides the higher rate of decrease in electric resistance between the electrodes relative to the increase of the deposition amount of PM and provides the higher rate of increase in electric current flowing between the electrodes. Whether the PM sensor is configured to generate the output value that reflects the resistance value between the electrodes or is configured to generate the output value that reflects the value of electric current flowing between the electrodes, the larger deposition amount of PM between the electrodes provides the higher variation in output value of the PM sensor relative to the increase of the deposition amount of PM.

When the deposition amount of PM between the electrodes reaches the effective deposition amount of PM and is then gradually increased by continuation of trapping PM, the output value of the PM sensor is gradually varied with the increase in deposition amount of PM. When extraneous substances as well as PM is trapped between the electrodes of the PM sensor, electrical continuity is established between the electrodes by the trapped extraneous substances to abruptly decrease the resistance value between the electrodes. In this case, the output value of the PM sensor is drastically varied, compared with the case where the output value of the PM sensor is varied with a gradual increase in deposition amount of PM between the electrodes by trapping PM between the electrodes. In other words, when the output value of the PM sensor is abruptly varied, there is a high possibility that extraneous substances are trapped between the electrodes of the PM sensor.

In the abnormality diagnosis apparatus of the above aspect, the monitor unit works to continuously monitor the output signal of the PM sensor after the PM deposition restart time. The PM deposition restart time denotes a time when deposition of PM between the electrodes of the PM sensor is restarted after completion of the sensor recovery process by the controller.

The estimated value of the deposition amount of PM between the electrodes of the PM sensor on the assumption that the filter is in the predetermined reference state is specified as the reference deposition amount of PM. The different state of the filter provides the different flow rate of PM from the filter. A change in flow rate of PM from the filter leads to a change in amount of PM trapped between the electrodes of the PM sensor and results in changing the deposition amount of PM between the electrodes. The reference state denotes a state of the filter assumed for estimation of the reference deposition amount of PM.

The variation in output value of the PM sensor per unit increase of the reference deposition amount of PM or the variation in output value of the PM sensor per unit time is specified as the sensor output change rate. When the output value of the PM sensor is drastically varied by trapping extraneous substances between the electrodes of the PM sensor as described above, this leads to an increase in sensor output change rate. Accordingly, when the sensor output change rate becomes higher than the predetermined determination change rate before elapse of the determination time period since the PM deposition restart time, the configuration of the present disclosure determines that the filter diagnosis process by the controller is not to be performed.

The determination change rate is used as a reference value for distinguishing whether the variation in output value of the PM sensor is to be attributed to the gradual increase in deposition amount of PM between the electrodes or is to be attributed to trapping of extraneous substances between the electrodes. Even in the case where the output value of the PM sensor is gradually varied by the gradual increase in deposition amount of PM between the electrodes, the sensor output change rate is not consistently constant. The larger deposition amount of PM between the electrodes provides the higher rate of decrease in resistance value between the electrodes relative to the increase in deposition amount of PM. The larger deposition amount of PM between the electrodes provides the higher rate of increase in electric current flowing between the electrodes relative to the increase in deposition amount of PM. Accordingly, the larger deposition amount of PM between the electrodes provides the higher variation in output value of the PM sensor relative to the increase in deposition amount of PM. After the PM deposition restart time, the deposition amount of PM between the electrodes is gradually increased by continuously trapping PM between the electrodes of the PM sensor. Even when substantially no extraneous substances are trapped between the electrodes, the sensor output change rate is thus gradually increased with an increase in deposition amount of PM between the electrodes.

It is assumed that the determination change rate is fixed to a relatively small value. In the state that a relatively large amount of PM deposits between the electrodes of the PM sensor, even when substantially no extraneous substances are trapped between the electrodes, the sensor output change rate by the change of the output value of the PM sensor attributed to an increase in deposition amount of PM between the electrodes may exceed the determination change rate. In this case, despite that substantially no extraneous substances are trapped between the electrodes of the PM sensor, the controller determines that the filter diagnosis process is not to be performed. It is assumed, on the other hand, that the determination change rate is fixed to a relatively large value. Even in the state that extraneous substances are trapped between the electrodes of the PM sensor, in the case where the sensor output change rate by the change in the output value of the PM sensor attributed to such trapping is relatively small, the sensor output change rate may not exceed the determination change rate. In this case, despite that extraneous substances are trapped between the electrodes of the PM sensor, the controller does not determine that the filter diagnosis process is not to be performed. As a result, the filter diagnosis process is performed.

According to the above aspect of the present disclosure, a higher value is set to the determination change rate that is to be compared with the sensor output change rate for determining whether the filter diagnosis process is to be performed or not, in the case where the deposition amount of PM between the electrodes of the PM sensor at the corresponding time to the sensor output change rate is expected to be large, compared with the case where the deposition amount of PM is expected to be small. This configuration can distinguish with the higher accuracy whether the variation in output value of the PM sensor is to be attributed to the gradual increase in deposition amount of PM between the electrodes or is to be attributed to trapping of extraneous substances between the electrodes.

Even when a relatively large deposition amount of PM between the electrodes of the PM sensor provides a relatively high sensor output change rate by the change in the output value of the PM sensor attributed to an increase in deposition amount of PM between the electrodes, this decreases the likelihood that the sensor output change rate exceeds the determination change rate. This accordingly suppresses the controller from determining that the filter diagnosis process is not to be performed, despite that substantially no extraneous substances are trapped between the electrodes of the PM sensor. Even when a relatively small deposition amount of PM between the electrodes of the PM sensor provides a relatively low output change rate by the change in the output value of the PM sensor attributed to trapping of extraneous substances between the electrodes, this increases the likelihood that the sensor output change rate exceeds the determination change rate. This accordingly increases the likelihood that the controller determines that the filter diagnosis process is not to be performed when extraneous substances are trapped between the electrodes of the PM sensor.

As described above, when extraneous substances are trapped between the electrodes of the PM sensor before elapse of the determination time period since the PM deposition restart time, the filter diagnosis process is not to be preformed. This can reduce wrong diagnosis by the controller that the filter is abnormal, due to trapping of extraneous substances between the electrodes of the PM sensor, despite that the filter is actually normal. This accordingly improves the diagnosis accuracy in the filter abnormality diagnosis using the output value of the PM sensor. Additionally, this can suppress execution of the filter abnormality diagnosis from being unnecessarily prohibited. This results in suppressing reduction of the execution frequency of the filter abnormality diagnosis beyond necessity.

The deposition amount of PM between the electrodes of the PM sensor may be expected to be large in the following cases. The deposition amount of PM between the electrodes of the PM sensor is expected to be large in the case where the reference deposition amount of PM is large, compared with the case where the reference deposition amount of PM is small. With regard to the PM sensor that is configured to provide an output value corresponding to the value of electric current flowing between the electrodes, the deposition amount of PM between the electrodes of the PM sensor is expected to be large in the case where the PM sensor has a large output value, compared with the case where the PM sensor has a small output value. With regard to the PM sensor that is configured to provide an output value corresponding to the value of resistance between the electrodes, the deposition amount of PM between the electrodes of the PM sensor is expected to be large in the case where the PM sensor has s small output value, compared with the case where the PM sensor has a large output value. The deposition amount of PM between the electrodes of the PM sensor is expected to be large in the case where a long time has elapsed since the PM deposition restart time, compared with the case where a short time has elapsed.

In the abnormality diagnosis apparatus of the above aspect, when the sensor output change rate is the variation in the output value of the PM sensor monitored by the monitor unit per unit increase in the reference deposition amount of PM, the controller may set a higher value to the determination change rate, which is to be compared with the sensor output change rate, in a case where the reference deposition amount of PM is large at the corresponding time to the sensor output change rate, compared with a case where the reference deposition amount of PM is small at the corresponding time to the sensor output change rate.

In the abnormality diagnosis apparatus of the above aspect, the sensor output change rate may be the variation in the output value of the PM sensor monitored by the monitor unit per unit increase in the reference deposition amount of PM and is calculated as a ratio of a difference between output values of the PM sensor at two times that are different from each other by a predetermined interval to a difference between reference deposition amounts of PM at the two times. An output value at an earlier time between output values of the PM sensor at two times used to calculate the sensor output change rate is specified as a first output value. In this aspect, when the PM sensor is configured to provide an output value corresponding to a value of electric current flowing between the electrodes and to increase the output value with an increase in deposition amount of PM between the electrodes, the controller may set a higher value to the determination change rate, which is to be compared with the sensor output change rate, in a case where the first output value used to calculate the sensor output change rate is large, compared with a case where the first output value is small. In the above aspect, when the PM sensor is configured to provide an output value corresponding to a value of resistance between the electrodes and to decrease the output value with an increase in deposition amount of PM between the electrodes, the controller may set a higher value to the determination change rate, which is to be compared with the sensor output change rate, in a case where the first output value used to calculate the sensor output change rate is small, compared with a case where the first output value is large.

In the abnormality diagnosis apparatus of the above aspect, when the sensor output change rate is the variation in the output value of the PM sensor monitored by the monitor unit per unit time, the controller may set a higher value to the determination change rate, which is to be compared with the sensor output change rate, in a case where a long time has elapsed since the PM deposition restart time, compared with a case where a short time has elapsed since the PM deposition restart time.

These aspects cause a higher value to be set to the determination change rate in the case where the deposition amount of PM between the electrodes of the PM sensor is expected to be large at the corresponding time to the sensor output change rate, compared with the case where the deposition amount of PM is expected to be small.

The abnormality diagnosis apparatus for the filter according to the above aspect of the present disclosure may further include a differential pressure sensor that is configured to output a signal corresponding to a difference in exhaust pressure between upstream and downstream the filter. And, the controller may further perform a filter recovery process, the filter recovery process being a process of removing PM depositing on the particulate filter. In this aspect, a state of the filter may be estimated based on an output value of the differential pressure sensor at a time when the filter recovery process performed by the controller is completed prior to execution of the sensor recovery process by the controller. The reference deposition amount of PM may be estimated on the assumption that the filter is in the estimated state predetermined as the reference state. This allows for estimation of the reference deposition amount of PM on the assumption that the state of the filter is close to the actual state to some extent. In this aspect, the sensor output change rate may be a variation in output value of the PM sensor monitored by the monitor unit per unit increase of the reference deposition amount of PM. This enables the variation in output value of the PM sensor attributed to the gradual increase of the deposition amount of PM between the electrodes to be distinguished from the variation in output value of the PM sensor attributed to trapping of extraneous substances between the electrodes, with the higher accuracy based on the sensor output change rate.

The above aspects of the present disclosure can improve the accuracy of abnormality diagnosis of the filter using the output value of the PM sensor provided downstream of the filter in the exhaust passage. This can also suppress reduction of the execution frequency of filter abnormality diagnosis beyond necessity.

Further features of the present disclosure will become apparent from the following description of exemplary embodiments with reference to the attached drawings.

DETAILED DESCRIPTION

The following describes embodiments of the present disclosure with reference to the drawings. The dimensions, the materials, the shapes, the positional relationships and the like of the respective components described in the following embodiments are only for the purpose of illustration and not intended at all to limit the scope of the present disclosure to such specific descriptions.

<Embodiment 1>

Figure 1:
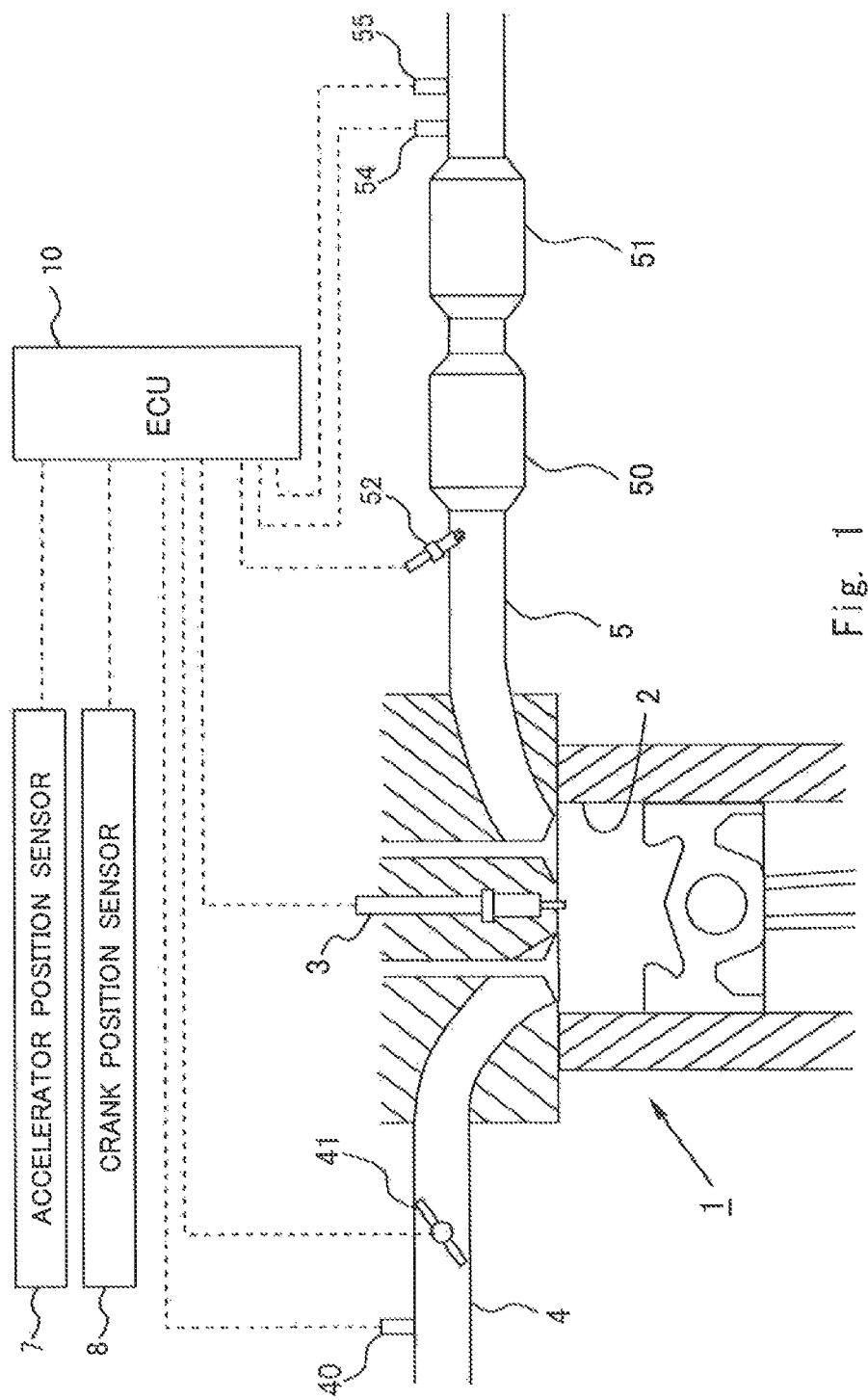
FIG. 1 is a first diagram illustrating the schematic configuration of an internal combustion engine and its intake and exhaust system according to an embodiment.

FIG. 1 is a diagram illustrating the schematic configuration of an internal combustion engine 1 and its intake and exhaust system according to an embodiment. The internal combustion engine 1 shown in FIG. 1 is a compression ignition internal combustion engine (diesel engine) using light oil as fuel. The internal combustion engine 1 may alternatively be a spark ignition internal combustion engine using gasoline or the like as fuel.

The internal combustion engine 1 includes a fuel injection valve 3 that is configured to inject the fuel into a cylinder 2. In the case of the internal combustion engine 1 provided as the spark ignition internal combustion engine, the fuel injection valve 3 may be configured to inject the fuel into an intake port.

The internal combustion engine 1 is connected with an intake passage 4. The intake passage 4 is provided with an air flow meter 40 and an intake throttle valve 41. The air flow meter 40 is configured to output an electric signal corresponding to the amount (mass) of the intake air (the air) flowing in the intake passage 4. The intake throttle valve 41 is placed downstream of the air flow meter 40 in the intake passage 4. The intake throttle valve 41 is configured to change the passage cross-sectional area of the intake passage 4 and thereby regulate the amount of the air taken into the internal combustion engine 1.

The internal combustion engine 1 is also connected with an exhaust passage 5. The exhaust passage 5 is provided with an oxidation catalyst 50 and a particulate filter (hereinafter simply referred to as "filter") 51. The filter 51 is placed downstream of the oxidation catalyst 50 in the exhaust passage 5. The filter 51 is a wall-flow filter that is made of a porous base material and is configured to trap PM included in the exhaust gas.

A fuel addition valve 52 is placed upstream of the oxidation catalyst 50 in the exhaust passage 5. The fuel addition valve 52 is configured to add the fuel to the exhaust gas flowing in the exhaust passage 5. The exhaust passage 5 is also provided with a temperature sensor 54 and a PM sensor 55 that are located downstream of the filter 51. The temperature sensor 54 is configured to output an electric signal corresponding to the temperature of the exhaust gas. The PM sensor 55 is configured to output an electric signal relating to the amount of PM flowing out of the filter 51.

Figure 2:
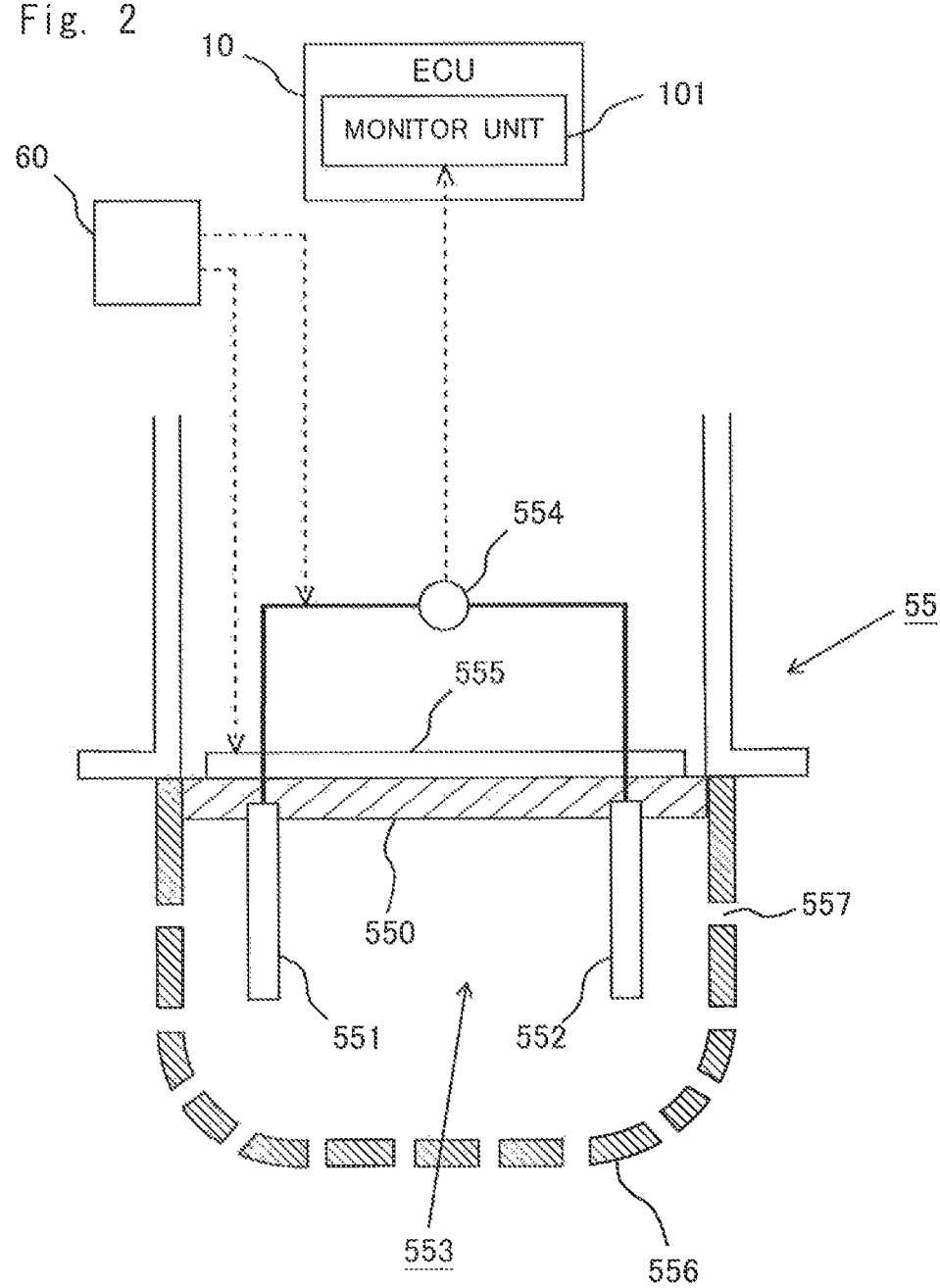
FIG. 2 is a diagram schematically illustrating the configuration of a PM sensor according to the embodiment.

The schematic configuration of the PM sensor 55 is described with reference to FIG. 2. FIG. 2 is a diagram illustrating the schematic configuration of the PM sensor 55. The PM sensor 55 is an electrode-based PM sensor. The PM sensor 55 includes only one set of electrodes in the illustrated example of FIG. 2 but may include multiple sets of electrodes.

The PM sensor 55 includes a sensor element 553, an ammeter 554, a heater 555 and a cover 556. The sensor element 553 is configured by a pair of electrodes 551 and 552 that are placed away from each other on a surface of a plate-like insulator 550. The ammeter 554 is configured to measure the electric current flowing between the electrodes 551 and 552. The heater 555 is an electric heater placed on a rear face of the insulator 550. The cover 556 is provided to cover the sensor element 553. The cover 556 has a plurality of through holes 557 formed therein. Electric power is supplied from an external power source 60 to the electrodes 551 and 552 and the heater 555 of the PM sensor 55. The PM sensor 55 provides an output value that reflects the value of electric current measured by the ammeter 554. The output value of the PM sensor 55 is input into a monitor unit 101 of an ECU 10. According to this embodiment, the output value of the PM sensor 55 may thus be continuously monitored by the monitor unit 101 of the ECU 10. In the case where the PM sensor 55 is provided with a sensor control unit (SCU) of controlling the PM sensor 55, the SCU may include a monitor unit configured to continuously monitor the output value of the PM sensor 55.

In the state that the PM sensor 55 having the above configuration is mounted to the exhaust passage 5, part of the exhaust gas flowing in the exhaust passage 5 flows into the cover 556 via the through holes 557. PM included in the exhaust gas flowing into the cover 556 is trapped between the electrodes 551 and 552. Trapping PM between the electrodes 551 and 552 is accelerated by applying a voltage to the electrodes 551 and 552.

Figure 3:
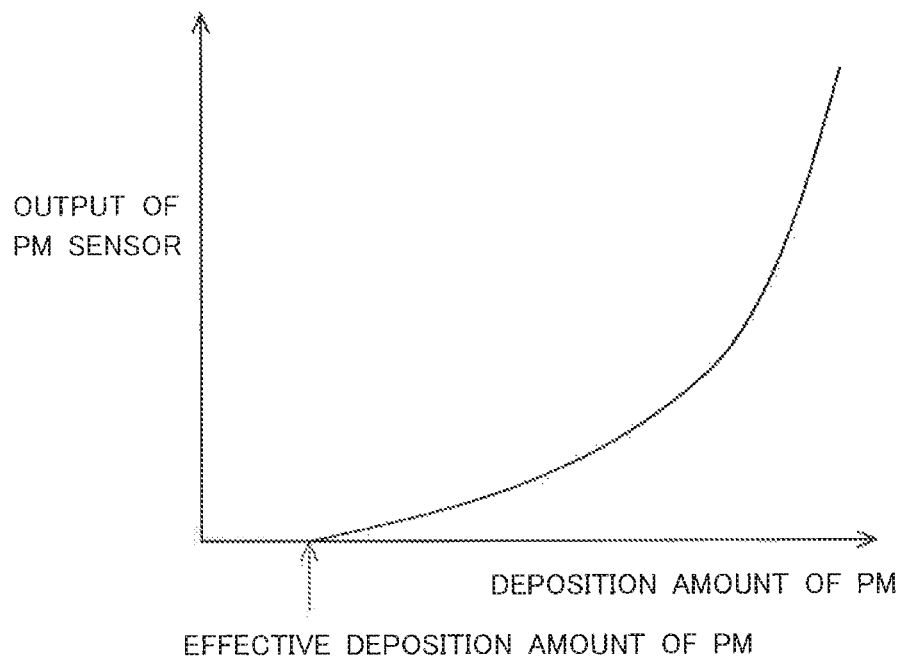
FIG. 3 is a diagram illustrating a relationship between the deposition amount of PM between electrodes of the PM sensor and the output value of the PM sensor according to the embodiment.

The following describes the relationship between the deposition amount of PM between the electrodes 551 and 552 and the output value of the PM sensor 55 with reference to FIG. 3. The abscissa of FIG. 3 shows the deposition amount of PM between the electrodes 551 and 552, and the ordinate of FIG. 3 shows the output value of the PM sensor 55. Trapping PM between the electrodes 551 and 552 results in gradually increasing the deposition amount of PM between the electrodes 551 and 552. In the state that a voltage is applied between the electrodes 551 and 552, deposition of a predetermined amount of PM between the electrodes 551 and 552 such as to connect from one electrode 551 to the other electrode 552 provides electrical continuity between the electrodes 551 and 552, due to the electrical conductivity of PM. When the deposition amount of PM between the electrodes 551 and 552 is less than the predetermined amount, however, there is no electrical continuity between the electrodes 551 and 552. The deposition amount of PM that provides electrical continuity between the electrodes 551 and 552 is hereinafter referred to as "effective deposition amount of PM".

As shown in FIG. 3, there is no electrical continuity between the electrodes 551 and 552 until the deposition amount of PM between the electrodes 551 and 552 reaches the effective deposition amount of PM, so that the output value of the PM sensor 55 is equal to zero. When the deposition amount of PM between the electrodes 551 and 552 reaches the effective deposition amount of PM, the output value of the PM sensor 55 becomes greater than zero. After the deposition amount of PM between the electrodes 551 and 552 reaches the effective deposition amount of PM, the electric resistance between the electrodes 551 and 552 decreases with an increase in deposition amount of PM between the electrodes 551 and 552. This results in increasing the electric current flowing between the electrodes 551 and 552. The output value of the PM sensor 55 accordingly increases with an increase in deposition amount of PM between the electrodes 551 and 552. In the description below, the time when the output value of the PM sensor 55 starts increasing from zero is called "output starting time". The larger deposition amount of PM between the electrodes 551 and 552 provides the higher rate of decrease in electric resistance between the electrodes 551 and 552 relative to the increase in deposition amount of PM and thereby provides the higher rate of increase in electric current flowing between the electrodes 551 and 552. The larger deposition amount of PM between the electrodes 551 and 552 accordingly provides the higher rate of increase in output value of the PM sensor 55 relative to the increase in deposition amount of PM.

Referring back to FIG. 1, the internal combustion engine 1 is provided with the electronic control unit (ECU) 10. The ECU 10 is a unit serving to control, for example, the operating conditions of the internal combustion engine 1. The ECU 10 is electrically connected with various sensors including an accelerator positions sensor 7 and a crank position sensor 8, in addition to the air flow meter 40, the temperature sensor 54 and the PM sensor 55 described above. The accelerator position sensor 7 is provided as a sensor that outputs an electric signal related to the operation amount (accelerator position) of an accelerator pedal (not shown). The crank position sensor 8 is provided as a sensor that outputs an electric signal related to the rotational position of an output shaft (crankshaft) of the internal combustion engine 1. The output signals of these sensors are input into the ECU 10. The ECU 10 is also electrically connected with various devices such as the fuel injection valve 3, the intake air throttle valve 41 and the fuel addition valve 52 described above. The ECU 10 controls the above various devices, based on the output signals from the above various sensors. For example, the ECU 10 performs a filter recovery process to remove PM depositing on the filter 51 by addition of the fuel by the fuel addition valve 52. The filter recovery process increases the temperature of the filter 51 with the heat generated by oxidation of the fuel added by the fuel addition valve 52 in the oxidation catalyst 50. This results in oxidizing and removing PM depositing on the filter 51.

[Filter Abnormality Diagnosis]

A failure such as breakage or erosion may occur in the filter 51 due to, for example, a temperature rise during the above filter recovery process. Such a failure occurring in the filter 51 or an abnormality of filter, for example, detachment of the filter 51 from the exhaust passage 5, increases PM released to the atmosphere. This embodiment accordingly performs filter abnormality diagnosis to determine whether the filter has any abnormality, based on the output value of the PM sensor 55. The following describes a procedure of filter abnormality diagnosis according to the embodiment.

The procedure of filter abnormality diagnosis according to this embodiment first performs a sensor recovery process, in order to remove PM depositing between the electrodes 551 and 552 of the PM sensor 55. More specifically, the sensor recovery process supplies electric power from the power source 60 to the heater 555, so as to heat the sensor element 553 by means of the heater 555. This results in oxidizing and removing PM depositing between the electrodes 551 and 552. In the sensor recovery process, the temperature of the sensor element 553 is controlled to a temperature that allows for oxidation of PM by adjusting the supply amount of electric power to the heater 555.

After performing the sensor recovery process to remove PM depositing between the electrodes 551 and 552, the procedure subsequently starts applying a voltage from the power source 60 to the electrodes 551 and 552. In the description below, the time when applying a voltage to the electrodes 551 and 552 is started is called "voltage applying time". The electrodes 551 and 552 have high temperature for some time after completion of the sensor recovery process. A cooling time period for cooling down the electrodes 551 and 552 may thus be provided between completion of the sensor recovery process and the voltage applying time.

As described above, applying a voltage to the electrodes 551 and 552 accelerates trapping PM between the electrodes 551 and 552. According to this embodiment, the voltage applying time thus corresponds to the PM deposition restart time of the present disclosure. According to this embodiment, applying a voltage to the electrodes 551 and 552 may be started during the sensor recovery process. In this case, the time when the sensor recovery process is completed (i.e., the time when power supply to the heater 555 is stopped) may be specified as the PM deposition restart time of the present disclosure. The time when a predetermined time period for determining that the temperature of the electrodes 551 and 552 of the PM sensor 55 is decreased to such a degree that does not oxidize the trapped PM has elapsed since completion of the sensor recovery process may be specified as the PM deposition restart time of the present disclosure.

Figure 4:
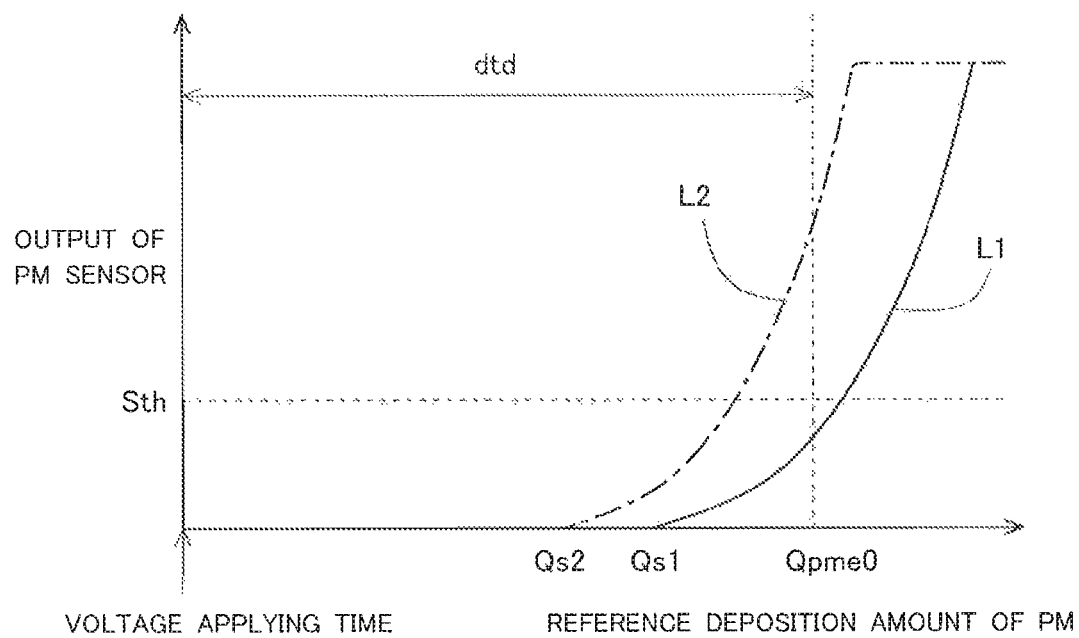
FIG. 4 is a diagram showing a variation in output value of the PM sensor after a voltage applying time according to the embodiment.

The following describes a behavior of the output value of the PM sensor 55 after a start of applying a voltage to the electrodes 551 and 552. FIG. 4 is a diagram showing a variation in output value of the PM sensor 55 after the voltage applying time. The abscissa of FIG. 4 shows a reference deposition amount of PM between the electrodes 551 and 552 of the PM sensor 55 after the voltage applying time, and the ordinate of FIG. 4 shows the output value of the PM sensor 55.

According to this embodiment, the reference deposition amount of PM is an estimated value on the assumption that the filter 51 is in a reference failure state. The reference failure state denotes a state of a slightest failure among the states that the filter 51 is to be determined as abnormal by filter abnormality diagnosis. Even in the state that the filter 51 deteriorates to some extent, when the deteriorating state is better than the reference failure state, the filter 51 is determined as normal by filter abnormality diagnosis. The reference deposition amount of PM is calculated by estimating the amount of PM trapped between the electrodes 551 and 552 of the PM sensor 55 (hereinafter simply referred to as "trapped amount of PM") on the assumption that the filter 51 is in the reference failure state and integrating the estimated value of the trapped amount of PM. Even in the case where the state of the filter 51 itself is unchanged, the amount of PM flowing out of the filter 51 is varied according to the operating conditions of the internal combustion engine 1 (for example, the amount of fuel injection from the fuel injection valve 3 and the flow rate of the exhaust gas) and the deposition amount of PM on the filter 51. The ratio of the amount of PM trapped between the electrodes 551 and 552 of the PM sensor 55 to the amount of PM included in the exhaust gas is also varied according to the flow rate of the exhaust gas. Estimation of the trapped amount of PM on the assumption that the filter 51 is in the reference failure state should accordingly take into account the operating conditions of the internal combustion engine 1 and the deposition amount of PM on the filter 51. Any known method may be employed to concretely calculate the reference deposition amount of PM.

In the graph of FIG. 4, a curve L1 shows a variation in output value of the PM sensor 55 in the normal state of the filter 51, and a curve L2 shows a variation in output value of the PM sensor 55 in the failed state of the filter 51. A variation in output value of the PM sensor 55 in the state that the filter 51 is detached from the exhaust passage 5 shows a similar tendency to the variation in the failed state of the filter 51 relative to the variation in the normal state of the filter 51. In the graph of FIG. 4, Qs1 represents a reference deposition amount of PM at the output starting time in the normal state of the filter 51, and Qs2 represents a reference deposition amount of PM at the output starting time in the failed state of the filter 51. The behavior of the output value of the PM sensor 55 as shown in FIG. 4 may be monitored by the monitor unit 101 of the ECU 10.

A failure of the filter 51 decreases the PM trapping efficiency of the filter 51. This results in increasing the amount of PM flowing out of the filter 51 per unit time (flow-out amount of PM). This accordingly increases the amount of PM that reaches the PM sensor 55 and is trapped between the electrodes 551 and 552. This leads to a higher increase rate of the deposition amount of PM between the electrodes 551 and 552. As a result, in the failed state of the filter 51, the deposition amount of PM between the electrodes 551 and 552 reaches the effective deposition amount of PM earlier than in the normal state of the filter 51. Accordingly, as shown in FIG. 4, the failed state of the filter 51 has a shorter time period from the voltage applying time to the output starting time than the normal state of the filter 51 (Qs2<Qs1). The failed state of the filter 51 also has a higher increase rate of the deposition amount of PM between the electrodes 551 and 552 after the output starting time than the normal state of the filter 51. The failed state of the filter 51 accordingly has a higher rate of change of the sensor output after the output starting time than the normal state of the filter 51 as shown in FIG. 4. The rate of change of the sensor output denotes an increase rate of the output value of the PM sensor 55 per unit increase of the reference deposition amount of PM.

There is a difference in behavior of the output value of the PM sensor 55 between the normal state of the filter 51 and the abnormal state of the filter 51 as described above. As a result, the abnormal state of the filter 51 provides a larger output value of the PM sensor 55 after elapse of a predetermined time period since the voltage applying time than the normal state of the filter 51. Accordingly, the procedure of filter abnormality diagnosis according to this embodiment reads the output value of the PM sensor 55 at the time when a predetermined determination time period dtd has elapsed since the voltage applying time. When the read output value of the PM sensor 55 is equal to or higher than a predetermined abnormality determination value Sth, it is determined that the PM sensor 55 is abnormal. The determination time period dtd is set as a time duration from the voltage applying time to the time when the reference deposition amount of PM reaches a predetermined determination amount of PM deposition Qpme0.

[Method of Determining Whether Filter Abnormality Diagnosis is to be Performed or not]

There is a likelihood that conductive materials other than PM as the original detection object (extraneous substances) are trapped between the electrodes 551 and 552 of the PM sensor 55. For example, moisture included in the exhaust gas is condensed to produce condensed water in the exhaust passage 5. The condensed water may enter the PM sensor 55 and may be trapped between the electrodes 551 and 552. In an application, the exhaust passage may be provided with a selective reduction NOx catalyst and a urea addition valve. The selective reduction NOx catalyst denotes a catalyst that uses ammonia as a reducing agent to reduce NOx in the exhaust gas. The urea addition valve is operated to add urea water for producing ammonia as the reducing agent to the exhaust gas. In a configuration that this urea addition valve is placed upstream of the PM sensor 55 in the exhaust passage 5, urea (urea deposit) precipitating from urea water may be trapped between the electrodes 551 and 552 of the PM sensor 55. Such condensed water and urea deposit are not the original detection object of the PM sensor 55 and should thus be regarded as extraneous substances.

According to this embodiment, part of PM included in the exhaust gas adheres to the wall surface of the exhaust passage 5 and various structures provided in the exhaust passage 5 such as the downstream-side end face of the filter 51 and the oxidation catalyst 50 (hereinafter referred to as "exhaust system structures"). The following phenomenon has also be found: PM once adhering to the wall surface of the exhaust passage 5 and the exhaust system structures and then falling off from the wall surface and the exhaust system structures (hereinafter referred to as "fall-off PM") may reach the PM sensor 55 and may be trapped between the electrodes 551 and 552. The original detection object of the PM sensor 55 is ordinary PM that is included in the exhaust gas discharged from the internal combustion engine 1 and reaches the PM sensor 55 without adhering to the wall surface of the exhaust passage 5 and the exhaust system structures. In other words, the fall-off PM is not the original detection object of the PM sensor 55. Accordingly, the fall-off PM is also a kind of extraneous substance, like the condensed water and the urea deposit described above.

Figure 5:
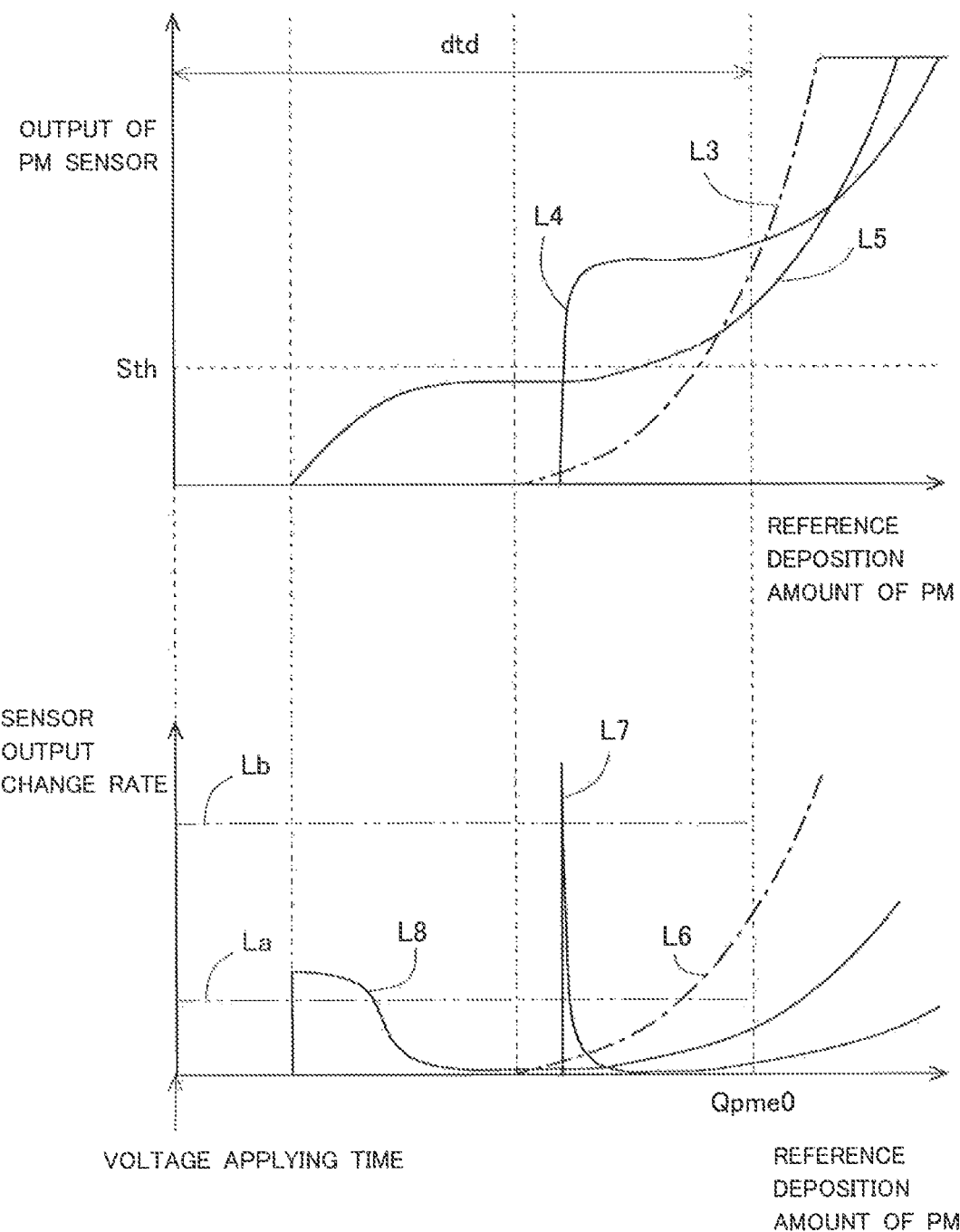
FIG. 5 is diagrams illustrating effect on the output value of the PM sensor by extraneous substances trapped between the electrodes of the PM sensor.

Even in the normal state of the filter 51, such extraneous substances are likely to be trapped between the electrodes 551 and 552 of the PM sensor 55. The following describes the effects of such extraneous substances trapped between the electrodes 551 and 552 of the PM sensor 55 on the output value of the PM sensor 55 with reference to FIG. 5. The upper graph of FIG. 5 is a diagram illustrating variations in output value of the PM sensor 55 after the voltage applying time. In the upper graph of FIG. 5, the abscissa shows the reference deposition amount of PM after the voltage applying time, and the ordinate shows the output value of the PM sensor 55. In the upper graph of FIG. 5, a curve L3 shows a variation in output value of the PM sensor 55 in the failed state of the filter 51. More specifically, the curve L3 shows a variation in output value of the PM sensor 55 in the case where the deposition amount of PM between the electrodes 551 and 552 is gradually increased by trapping the ordinary PM between the electrodes 551 and 552 of the PM sensor 55. In the upper graph of FIG. 5, both curves L4 and L5, on the other hand, show variations in output value of the PM sensor 55 in the normal state of the filter 51. More specifically, both the curves L4 and L5 show variations in output value of the PM sensor 55 in the case where the extraneous substances as well as the ordinary PM is trapped between the electrodes 551 and 552 of the PM sensor 55. The lower graph of FIG. 5 is a diagram illustrating variations in sensor output change rate of the PM sensor 55 after the voltage applying time. In the lower graph of FIG. 5, the abscissa shows the reference deposition amount of PM after the voltage applying time, and the ordinate shows the sensor output change rate. In the lower graph of FIG. 5, a curve L6 shows a variation in sensor output change rate corresponding to the variation in output value of the PM sensor 55 shown by the curve L3 in the upper graph of FIG. 5. In the lower graph of FIG. 5, a curve L7 shows a variation in sensor output change rate corresponding to the variation in output value of the PM sensor 55 shown by the curve IA in the upper graph of FIG. 5. In the lower graph of FIG. 5, a curve L8 shows a variation in sensor output change rate corresponding to the variation in output value of the PM sensor 55 shown by the curve L5 in the upper graph of FIG. 5.

When the extraneous substances are trapped between the electrodes 551 and 552 of the PM sensor 55, the trapped extraneous substances establish electrical continuity between the electrodes 551 and 552 and thereby drastically decrease the resistance value between the electrodes 551 and 552. Accordingly, in the case where the extraneous substances are trapped between the electrodes 551 and 552 before the deposition amount of PM between the electrodes 551 and 552 of the PM sensor 55 reaches the effective deposition amount of PM, the output value of the PM sensor 55 starts increasing from zero at this time. In this case, as shown by the curves L14 and L5 in the upper graph of FIG. 5, the output value of the PM sensor 55 abruptly increases at the output starting time. Compared with the case where the deposition amount of PM between the electrodes 551 and 552 is gradually increased to exceed the effective deposition amount of PM, the output value of the PM sensor 55 drastically increases at the output starting time in this case. As a result, the output value of the PM sensor 55 is likely to become larger than the abnormality determination value Sth at the time when the determination time period dtd has elapsed since the voltage applying time, despite that the filter 51 is actually normal.

Accordingly, in the case where the extraneous substances are trapped between the electrodes 551 and 552 of the PM sensor 55 before elapse of the predetermined determination time period dtd since the voltage applying time, in the process of filter abnormality diagnosis using the output value of the PM sensor 55 as described above, there is a likelihood of wrong diagnosis that the filter 51 is abnormal, despite that the filter 51 is actually normal.

According to this embodiment, the output signal of the PM sensor 55 after the voltage applying time is continuously monitored by the monitor unit 101 of the ECU 10. The reference deposition amount of PM after the voltage applying time is also continuously estimated by the ECU 10. The procedure of this embodiment determines whether filter abnormality diagnosis using the output value of the PM sensor 55 is to be prohibited or not, based on the sensor output change rate after the voltage applying time calculated from the output value of the PM sensor 55 and the estimated reference deposition amount of PM. More specifically, in the case where the sensor output change rate becomes higher than a predetermined determination change rate after the output starting time, the procedure of this embodiment determines that a filter diagnosis process of diagnosing an abnormality of the filter 51 based on the output value of the PM sensor 55 at the time when the determination time period dtd has elapsed since the voltage applying time is not to be performed.

As described above, in the case where the extraneous substances are trapped between the electrodes 551 and 552 of the PM sensor 55, the output value of the PM sensor 55 abruptly increases, compared with the case where the deposition amount of PM between the electrodes 551 and 552 is gradually increased by trapping PM between the electrodes 551 and 552. Accordingly, as shown by the curves L7 and L8 in the lower graph of FIG. 5, the sensor output change rate in the case where the extraneous substances are trapped between the electrodes 551 and 552 of the PM sensor 55 becomes higher than the sensor output change rate in the case where the deposition amount of PM between the electrodes 551 and 552 is gradually increased. In other words, when the sensor output change rate is drastically increased after the output starting time, it is determinable that there is a high possibility that the extraneous substances are trapped between the electrodes 551 and 552 of the PM sensor 55. In this case, the procedure of this embodiment determines that the filter diagnosis process is not to be performed.

Even in the case where the output value of the PM sensor 55 is gradually varied by the gradual increase in deposition amount of PM between the electrodes 551 and 552, the sensor output change rate is not consistently constant. As described above, the larger deposition amount of PM between the electrodes 551 and 552 provides the higher rate of increase in output value of the PM sensor 55 relative to the increase in deposition amount of PM. In general, the amount of PM actually depositing between the electrodes 551 and 552 increases with an increase in reference deposition amount of PM. Accordingly, as shown by the curve L6 in the lower graph of FIG. 5, the sensor output change rate gradually increases with an increase in reference deposition amount of PM even when substantially no extraneous substances are trapped between the electrodes 551 and 552.

It is assumed that the determination change rate is fixed to a relatively small value like La shown in the lower graph of FIG. 5. The sensor output change rate may exceed the determination change rate La at the relatively large deposition amount of PM between the electrodes 551 and 552 of the PM sensor 55 (i.e., at the relatively large reference deposition amount of PM) as shown by the curve L6 in the lower graph of FIG. 5. In other words, even when substantially no extraneous substances are trapped between the electrodes 551 and 552, the sensor output change rate by the change in the output value of the PM sensor 55 attributed to an increase in deposition amount of PM between the electrodes 551 and 552 may exceed the determination change rate La. In this case, it is determined that the filter diagnosis process is not to be performed, despite that substantially no extraneous substances are trapped between the electrodes 551 and 552 of the PM sensor 55. As a result, as shown by the curve L3 in the upper graph of FIG. 5, a failure of the filter 51 is not detectable despite a variation in output value of the PM sensor 55 that indicates a failure of the filter 51.

It is assumed, on the other hand, that the determination change rate is fixed to a relatively large value like Lb shown in the lower graph of FIG. 5. When the sensor output change rate by the increase in the output value of the PM sensor 55 attributed to trapping of extraneous substances between the electrodes 551 and 552 of the PM sensor 55 is as large as shown by the curve L7 in the lower graph of FIG. 5, The sensor output change rate exceeds the determination change rate Lb. In this case, it is determined that the filter diagnosis process is not to be performed. There is, however, a possibility that the sensor output change rate by the increase in the output value of the PM sensor 55 attributed to trapping of extraneous substances between the electrodes 551 and 552 of the PM sensor 55 is relatively small. In other words, the sensor output change rate may not exceed the determination change rate Lb, despite that the extraneous substances are trapped between the electrodes 551 and 552 of the PM sensor 55. In this case, it is not determined that the filter diagnosis process is not to be performed, despite that the extraneous substances are trapped between the electrodes 551 and 552 of the PM sensor 55. As a result, the filter diagnosis process is performed to provide a wrong diagnosis that the filter 51 is abnormal, despite that the filter 51 is actually normal.

Figure 6:
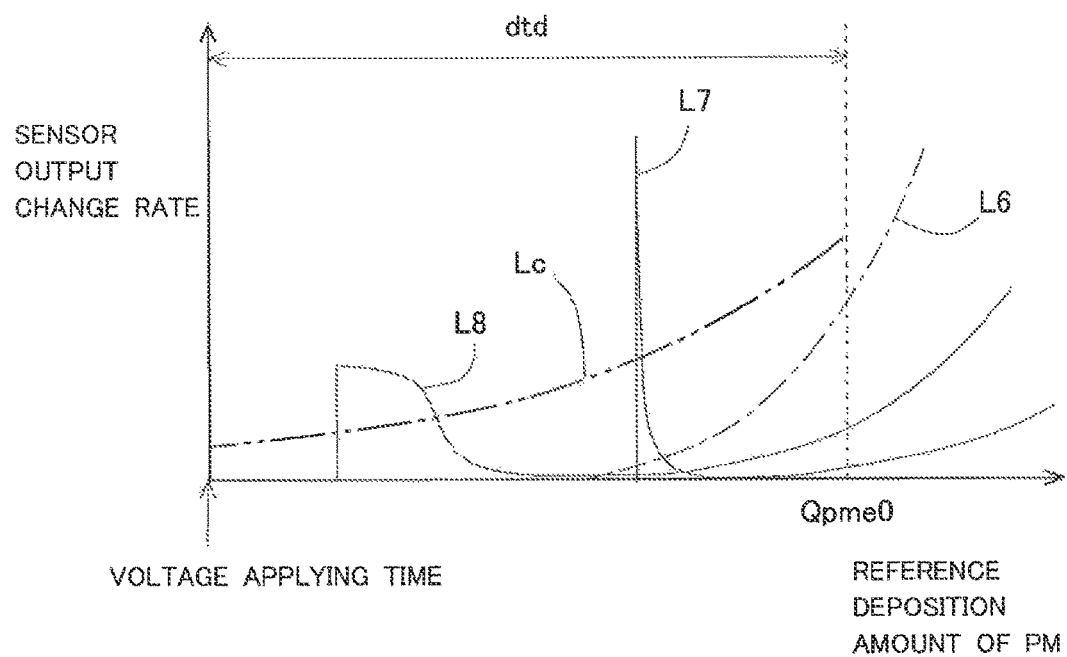
FIG. 6 is a diagram illustrating a correlation between reference deposition amount of PM and determination change rate according to the embodiment.

This embodiment thus changes the determination change rate that is to be compared with the sensor output change rate for determination of whether the filter diagnosis process is to be performed or not, according to reference deposition amount of PM at the corresponding time to the sensor output change rate. FIG. 6 is a diagram illustrating a correlation between the reference deposition amount of PM and the determination change rate according to the embodiment. In the graph of FIG. 6, the abscissa shows the reference deposition amount of PM, and the ordinate shows the sensor output change rate. Like the curves L6, L7 and L8 in the lower graph of FIG. 5, curves L6, L7 and L8 in the graph of FIG. 6 respectively show variations in sensor output change rate corresponding to the variations in output value of the PM sensor 55 shown by the curves L3, L4 and L5 in the upper graph of FIG. 5. A curve Lc in FIG. 6 shows a correlation between the reference deposition amount of PM and the determination change rate. As shown by this curve Lc in FIG. 6, according to this embodiment, the determination change rate is set to increase with an increase in reference deposition amount of PM.

Setting the determination change rate based on the reference deposition amount of PM as described above causes a higher value to be set to the determination change rate in the case where the amount of PM actually depositing between the electrodes 551 and 552 of the PM sensor 55 is expected to be large at the corresponding time to the sensor output change rate, compared with the case where the deposition amount of PM is expected to be small. As shown by the curve L6 in FIG. 6, this suppresses the sensor output change rate from exceeding the determination change rate even when a relatively large amount of PM depositing between the electrodes 551 and 552 of the PM sensor 55 causes an increase in output value of the PM sensor 55 attributed to an increase in deposition amount of PM between the electrodes 551 and 552 to provide a relatively high sensor output change rate. This accordingly reduces inadequate determination that the filter diagnosis process is not to be performed, despite that substantially no extraneous substances are trapped between the electrodes 551 and 552 of the PM sensor 55.

A relatively small amount of PM depositing between the electrodes 551 and 552 of the PM sensor 55, on the other hand, increases the likelihood that the sensor output change rate exceeds the determination change rate even when a change in output value of the PM sensor 55 attributed to trapping of extraneous substances between the electrodes 551 and 552 provides a relatively low sensor output change rate, as shown by the curve L8 in FIG. 6. This accordingly increases the likelihood of determination that the filter diagnosis process is not to be performed when extraneous substances are trapped between the electrodes 551 and 552 of the PM sensor 55.

As described above, the procedure of the embodiment can distinguish with the higher accuracy whether the change in output value of the PM sensor 55 before elapse of the determination time period dtd since the voltage applying time is to be attributed to the gradual increase in deposition amount of PM between the electrodes 551 and 552 or is to be attributed to trapping of extraneous substances between the electrodes 551 and 552.

[Flow of Filter Abnormality Diagnosis]

Figure 7:
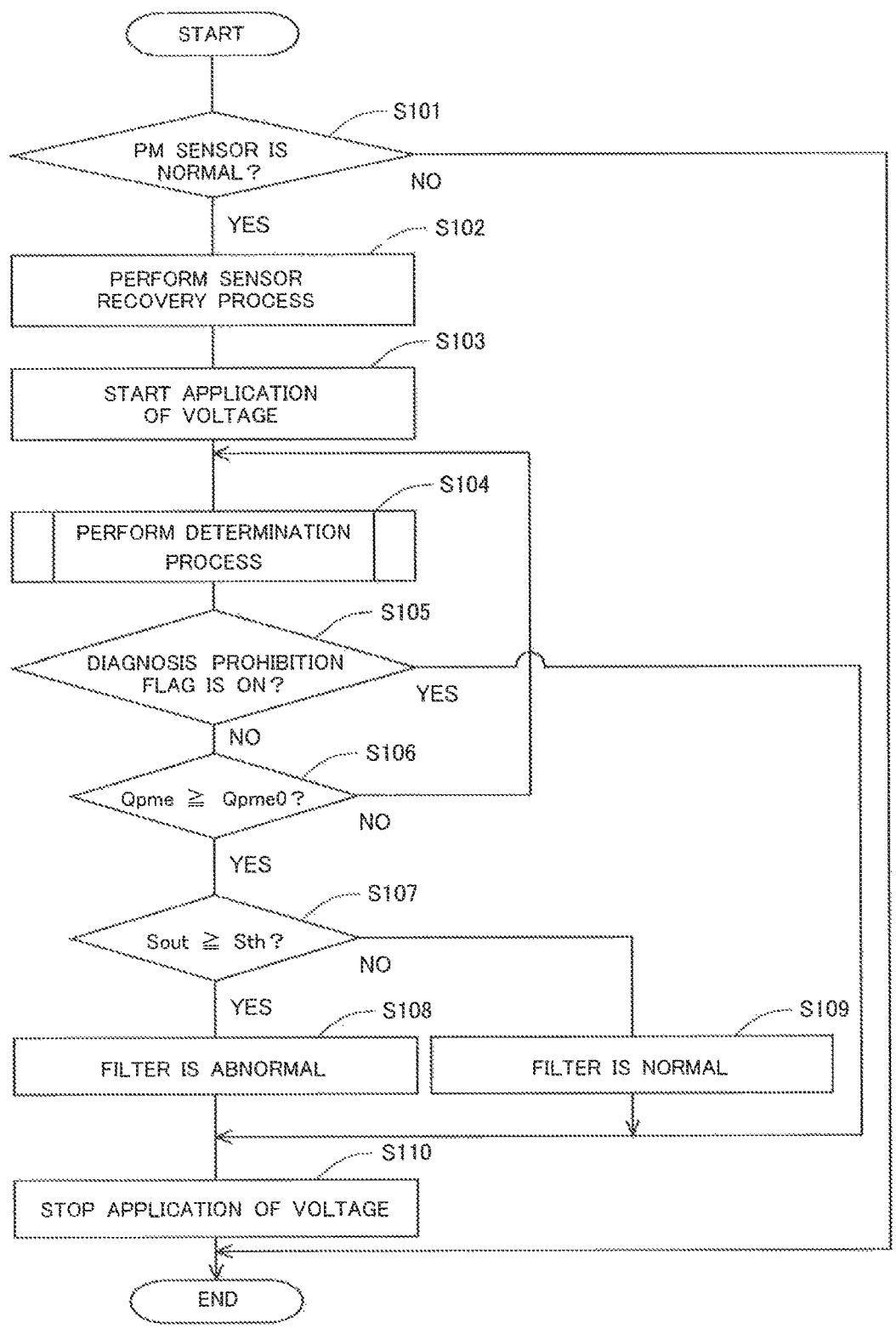
FIG. 7 is a flowchart showing a flow of filter abnormality diagnosis process according to the embodiment.

The following describes a flow of filter abnormality diagnosis of the embodiment with reference to FIG. 7. FIG. 7 is a flowchart showing the flow of filter abnormality diagnosis of the embodiment. This flow is performed by the ECU 10 on satisfaction of predetermined filter diagnosis preliminary conditions. The filter diagnosis preliminary conditions herein are conditions to perform the sensor recovery process prior to the filter diagnosis process. The filter diagnosis preliminary conditions are set to necessarily and sufficiently ensure the execution frequency of the filter diagnosis process. The filter diagnosis preliminary conditions may be, for example, that the internal combustion engine 1 is in the state of steady operation and that a predetermined time period has elapsed since previous execution of the filter diagnosis process or that a predefined time period has elapsed since a current start of operation of the internal combustion engine 1. In an application that the PM sensor 55 is provided with an SCU, this flow may be performed by the SCU.

This flow first determines whether the PM sensor 55 is normal at S101. According to this embodiment, a flow of failure diagnosis of the PM sensor 55 is performed as a separate routine from this flow, and the result of failure diagnosis is stored in the ECU 10. At S101, the flow reads the result of failure diagnosis of the PM sensor 55 stored in the ECU 10. When the result of diagnosis indicating a failure of the PM sensor 55 is stored in the ECU 10, a negative answer is provided at S101. In this case, the flow is terminated. When the result of diagnosis indicating a failure of the PM sensor 55 is not stored in the ECU 10, on the other hand, an affirmative answer is provided at S101. In this case, the flow proceeds to the process of S102. Any of known techniques may be employed for failure diagnosis of the PM sensor 55.

At S102, the sensor recovery process is performed. The sensor recovery process supplies electric power from the power source 60 to the heater 555 and controls the temperature of the sensor element 553 to a temperature that allows for oxidation of PM. At S102, the supply of electric power to the heater 555 is continued until elapse of a predetermined sensor recovery time since the start of power supply. The sensor recovery time may be a fixed value determined in advance by experiment or the like as a sufficient time duration for removal of PM depositing between the electrodes 551 and 552 of the PM sensor 55. The sensor recovery time may be set, based on an estimated deposition amount of PM between the electrodes 551 and 552 at the start of the sensor recovery process. When the sensor recovery time has elapsed since the start of supply of electric power to the heater 555, the supply of electric power from the power source 60 to the heater 555 is stopped, so that the sensor recovery process is completed. The deposition amount of PM between the electrodes 551 and 552 of the PM sensor 55 is approximately zero at the time when the sensor recovery process is completed.

The flow subsequently performs the process of S103. At S103, the flow starts application of a voltage to the electrodes 551 and 552 of the PM sensor 55. This accelerates trapping PM between the electrodes 551 and 552. According to this embodiment, at the start of application of a voltage to the electrodes 551 and 552 of the PM sensor 55, the monitor unit 101 of the ECU 10 starts monitoring the output value of the PM sensor 55. A cooling time period for cooling down the electrodes 551 and 552 may be provided between completion of the sensor recovery process and start of applying a voltage to the electrodes 551 and 552 of the PM sensor 55, as described above. The application start time of a voltage to the electrodes 551 and 552 of the PM sensor 55 may not be necessarily simultaneous with the monitor start time of the output value of the PM sensor 55 by the monitor unit 101 of the ECU 10.

Figure 8:
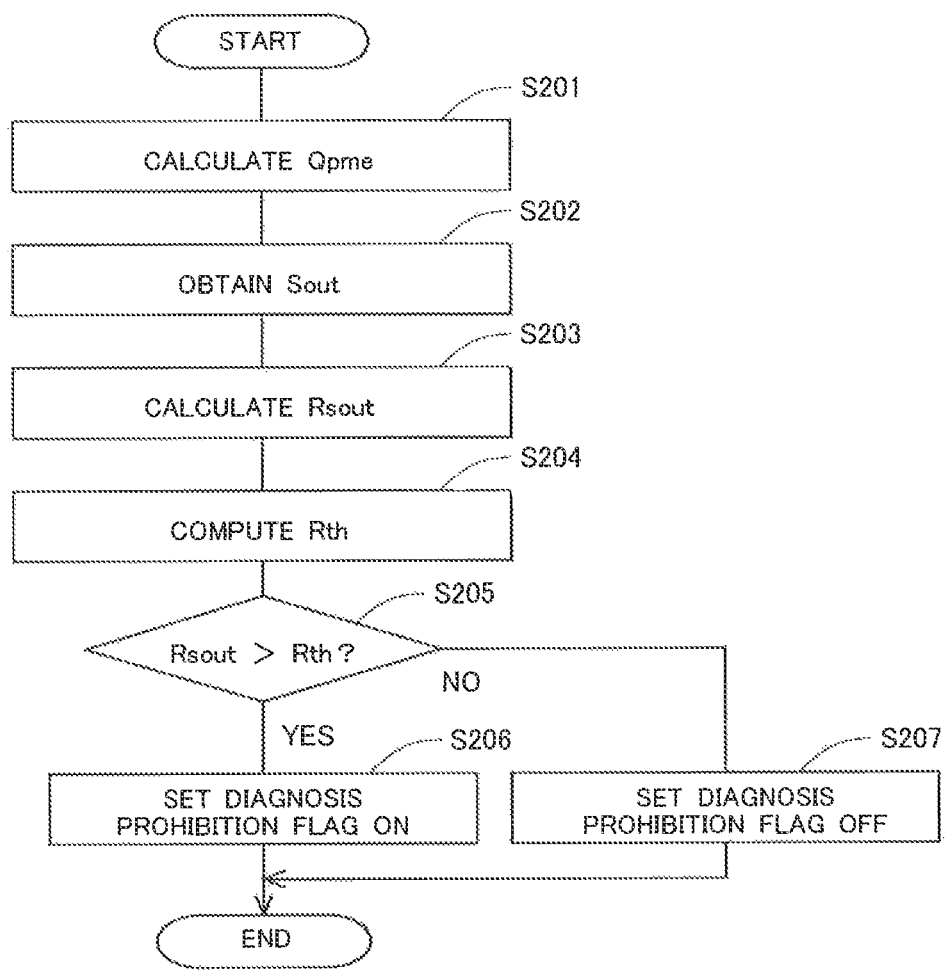
FIG. 8 is a flowchart sowing a flow of determination process to determine whether execution of a filter diagnosis process is to be prohibited or not according to the embodiment.

At S104, the flow subsequently performs a determination process of determining whether execution of the filter diagnosis process is to be prohibited. The following describes a flow of the determination process of the embodiment with reference to FIG. 8. FIG. 8 is a flowchart showing the flow of the determination process of the embodiment. This flow is repeatedly performed by the ECU 10 after start of application of a voltage to the electrodes 551 and 552 of the PM sensor 55. In the application that the PM sensor 55 is provided with an SCU, this flow may also be performed by the SCU.

At S201, the flow calculates a reference deposition amount of PM Qpme at the current moment. The reference deposition amount of PM Qpme is calculated, based on the operating conditions of the internal combustion engine 1 and the deposition amount of PM on the filter 51 on the assumption that the filter 51 is in the reference failure state. The deposition amount of PM on the filter 51 on the assumption that the filter 51 is in the reference failure state may be calculated by estimating the amount of PM trapped by the filter 51 on the assumption that the filter 51 is in the reference failure state and the removal amount of PM oxidized by increasing the temperature of the exhaust gas to be removed from the filter 51 and integrating these estimated values.

At S202, the flow subsequently obtains an output value Sout of the PM sensor 55 at the current moment. At S203, the flow then calculates a sensor output change rate Rsout of the PM sensor 55. In this calculation, the reference deposition amount of PM calculated at S201 in a previous cycle of this flow is defined as a first reference PM deposition amount Qpme1, and the reference deposition amount of PM calculated at S201 in a current cycle of this flow is defined as a second reference PM deposition amount Qpme2. The output value of the PM sensor obtained at S202 in the previous cycle of this flow is defined as a first output value Sout1, and the output value of the PM sensor obtained at S202 in the current cycle of this flow is defined as a second output value Sout2. At S203, the sensor output change rate Rsout is calculated according to Equation (1) given below:

$$Rsout=(Sout2-Sout1)/(Qpme2-Qpme1) \qquad (1)$$

The sensor output change rate Rsout is thus calculated as a ratio of the difference between the output values of the PM sensor at two different times of execution of this flow to the difference between the reference deposition amounts of PM at the two different times.

At S204, the flow subsequently computes a determination change rate Rth, based on the reference deposition amount of Qpme calculated at S201. According to this embodiment, a map representing the correlation between the reference deposition amount of PM and the determination change rate as shown by the curve Lc in FIG. 6 is stored in the ECU 10. The flow uses this map to compute the determination change rate Rth at S204. In this embodiment, the determination change rate Rth is computed, based on the second reference PM deposition amount Qpme2 out of the first reference PM deposition amount Qpme1 and the second reference PM deposition amount Qpme2 used for the calculation of the sensor output change rate Rsout at S203. The first reference PM deposition amount Qpme1 may also be regarded as the reference deposition amount of PM at the corresponding time to the sensor output change rate Rsout calculated at S203 in the current cycle. Accordingly, the determination change rate Rth may be computed, based on the first reference PM deposition amount Qpme1 at S204.

At S205, the flow subsequently determines whether the sensor output change rate Rsout calculated at S203 exceeds the determination change rate Rth computed at S204. In the case of an affirmative answer at S205, there is a high possibility that extraneous substances are trapped between the electrodes 551 and 552 of the PM sensor 55. In this case, it is determined that the filter diagnosis process based on the output value of the PM sensor 55 at the time when the determination time period dtd has elapsed since the voltage applying time is not to be performed. Accordingly, in the case of an affirmative answer at S205, the flow sets a diagnosis prohibition flag ON at S206. In the case of a negative answer at S205, i.e., when the sensor output change rate Rsout calculated at S203 is equal to or lower than the determination change rate Rth computed at S204, on the other hand, there is a high possibility that substantially no extraneous substances are trapped between the electrodes 551 and 552 at the current moment. In this case, the flow sets the diagnosis prohibition flag OFF at S207.

The description is referred back to the flow of filter abnormality diagnosis shown in FIG. 7. This flow performs the process of S105 after the process of S104. At S105, the flow determines whether the diagnosis prohibition flag is set ON by the determination process performed at S104. In the case of a negative answer at S105, i.e., when the diagnosis prohibition flag is OFF, the flow subsequently determines whether the current reference deposition amount of PM Qpme is equal to or larger than the determination amount of PM deposition Qpme0 at S106. This determines whether the determination time period dtd has elapsed since the voltage applying time. In the case of a negative answer at S106, the determination process is performed again at S104.

In the case of an affirmative answer at S106, on the other hand, it is determined that the determination time period dtd has elapsed since the voltage applying time without setting the diagnosis prohibition flag ON in the determination process at S104. In other words, it is determined that the determination time period dtd has elapsed since the voltage applying time while substantially no extraneous substances are trapped between the electrodes 551 and 552 of the PM sensor 55. In this case, it is determined that the filter diagnosis process based on the output value of the PM sensor 55 at the time when the determination time period dtd has elapsed since the voltage applying time is to be performed. In the case of the affirmative answer at S106, the flow accordingly performs the filter diagnosis process at S107. More specifically, the filter diagnosis process determines whether the output value Sout of the PM sensor 55 is equal to or larger than the abnormality determination value Sth when the reference deposition amount of PM Qpme reaches the determination amount of PM deposition Qpme0. In the case of an affirmative answer at S107, the flow determines that the filter 51 is abnormal at S108. In the case of a negative answer at S107, on the other hand, the flow determines that the filter 51 is not abnormal but is normal at S109. After determining that the filter 51 is abnormal at S108 or determining that the filter 51 is normal at S109, the flow stops application of a voltage to the electrodes 551 and 552 of the PM sensor 55 at S110.

In the case of an affirmative answer at S105, on the other hand, the flow subsequently stops application of a voltage to the electrodes 551 and 552 of the PM sensor 55 at S110. This accordingly stops application of a voltage to the electrodes 551 and 552 without performing the filter diagnosis process. In the case of an affirmative answer at S105, it is, however, not necessarily required to stop application of a voltage to the electrodes 551 and 552 of the PM sensor 55 immediately. Even in the case of an affirmative answer at S105, a modification may continue application of a voltage to the electrodes 551 and 552 until the reference deposition amount of PM Qpme reaches the determination amount of PM deposition Qpme0. This modification also determines that the filter diagnosis process based on the output value of the PM sensor 55 at the time when the reference deposition amount of PM Qpme reaches the determination amount of PM deposition Qpme0 is not to be performed. In the case of an affirmative answer at S105, another modification may perform the sensor recovery process to remove the extraneous substances trapped between the electrodes 551 and 552 and subsequently perform the processing of and after S103 again. Any processing flow that performs another process without performing the filter diagnosis process in the case of an affirmative answer at S105 corresponds to the "controller determining that the filter diagnosis process is not to be performed".

The flow of filter abnormality diagnosis described above determines that the filter diagnosis process is not to be performed in the case where extraneous substances are trapped between the electrodes 551 and 552 of the PM sensor 55 before elapse of the determination time period dtd since the voltage applying time. This can reduce wrong diagnosis that the filter 51 is abnormal in the filter diagnosis process, due to trapping of extraneous substances between the electrodes 551 and 552 of the PM sensor 55, despite that the filter 51 is actually normal. This results in improving the accuracy of diagnosis of the filter in the filter diagnosis process. Additionally, the above flow of filter abnormality diagnosis sets the determination change rate to increase with an increase in reference deposition amount of PM at the corresponding time to the sensor output change rate. This can suppress execution of the filter diagnosis process from being unnecessarily prohibited. This results in suppressing reduction of the execution frequency of abnormality diagnosis of the filter beyond necessity.

According to the embodiment described above, the PM sensor 55 is configured to provide the output value corresponding to the value of electric current flowing between the electrodes 551 and 552. The output value of the PM sensor 55 accordingly increases with an increase in deposition amount of PM between the electrodes 551 and 552. According to a modification, the PM sensor 55 may be configured to provide an output value that reflects the resistance value between the electrodes 551 and 552. In this modification, the output value of the PM sensor 55 decreases with an increase in deposition amount of PM between the electrodes 551 and 552. In this modification, at S203 in the flow of determination process shown in FIG. 8 to determine whether execution of the filter diagnosis process is to be prohibited or not, the sensor output change rate Rsout is calculated according to Equation (2) given below:

$$Rsout=(Sout1-Sout2)/(Qpme2-Qpme1) \quad (2)$$

In the PM sensor 55 configured to have the output characteristic that the output value of the PM sensor 55 decreases with an increase in deposition amount of PM between the electrodes 551 and 552, the larger deposition amount of PM between the electrodes 551 and 552 provides the higher rate of decrease in output value of the PM sensor 55 relative to the increase in deposition amount of PM. Accordingly, in this modification, the sensor output change rate gradually increases with an increase in reference deposition amount of PM even when substantially no extraneous substances are trapped between the electrodes 551 and 552.

According to the embodiment described above, the determination change rate is set to gradually increase with an increase in reference deposition amount of PM as shown by the curve Lc in FIG. 6. According to a modification, however, the determination change rate may be set to increase stepwise with an increase in reference deposition amount of PM. In general, a higher value is set to the determination change rate, which is to be compared with the sensor output change rate, in the case where the reference deposition amount of PM is large at the corresponding time to the sensor output change rate, compared with the case where the reference deposition amount of PM is small.

According to the embodiment described above, the sensor output change rate Rsout is calculated as the parameter used for filter abnormality diagnosis. According to a modification, a value correlated with the sensor output change rate may be used instead as the parameter. For example, a differential between a first output difference and a second output difference or a ratio of the first output difference to the second output difference may be used as the parameter of abnormality diagnosis. The first output difference denotes a difference between the first reference PM deposition amount Qpme1 and the first output value Sout1 of the PM sensor 55, which are used for calculation of the sensor output change rate Rsout in the flow of determination process shown in FIG. 8. The second output difference denotes a difference between the second reference PM deposition amount Qpme2 and the second output value Sout2 of the PM sensor 55, which are used for calculation of the sensor output change rate Rsout.

According to the embodiment described above, the reference deposition amount of PM is the estimated value on the assumption that the filter 51 is in the reference failure state. According to a modification, the reference deposition amount of PM may be an estimated value on the assumption that the filter 51 is not provided in the exhaust passage 5. In this modification, the determination amount of PM deposition used to specify the determination time period dtd and the abnormality determination value to be compared with the output value of the PM sensor 55 in the filter diagnosis process may also be set on the premise that the reference deposition amount of PM is the estimated value on the assumption that the filter 51 is not provided in the exhaust passage 5.

In the embodiment described above, as shown in FIG. 9, a differential pressure sensor 56 may be provided in the exhaust passage 5. The differential pressure sensor 56 outputs an electric signal corresponding to a difference in exhaust pressure between upstream and downstream of the filter 51. Like the output signals of the other sensors, the output signal of the differential pressure sensor 56 is input into the ECU 10. At the time of completion of the filter recovery process, i.e., in the state that substantially no PM deposits on the filter 51, the output value of the differential pressure sensor 56 is correlated with the state of the filter 51 to some extent. More specifically, under a fixed operating condition of the internal combustion engine 1, i.e., at a fixed flow rate of exhaust gas flowing into the filter 51, the difference in exhaust pressure between upstream and downstream of the filter 51 decreases with an increase in degree of deterioration of the filter 51. The higher degree of deterioration of the filter 51 accordingly provides the smaller output value of the differential pressure sensor 56. In the configuration that the differential pressure sensor 56 is provided in the exhaust passage 5, the state of the filter 51 may be estimated, based on the output value of the differential pressure sensor 56 at the time of completion of the filter recovery process. It is, however, difficult to estimate the state of the filter 51 with sufficient accuracy using only the output value of the differential pressure sensor 56. Even in the configuration with the differential pressure sensor 56, there is also a need for filter abnormality diagnosis using the output value of the PM sensor as described in the above embodiment.

Figure 9:
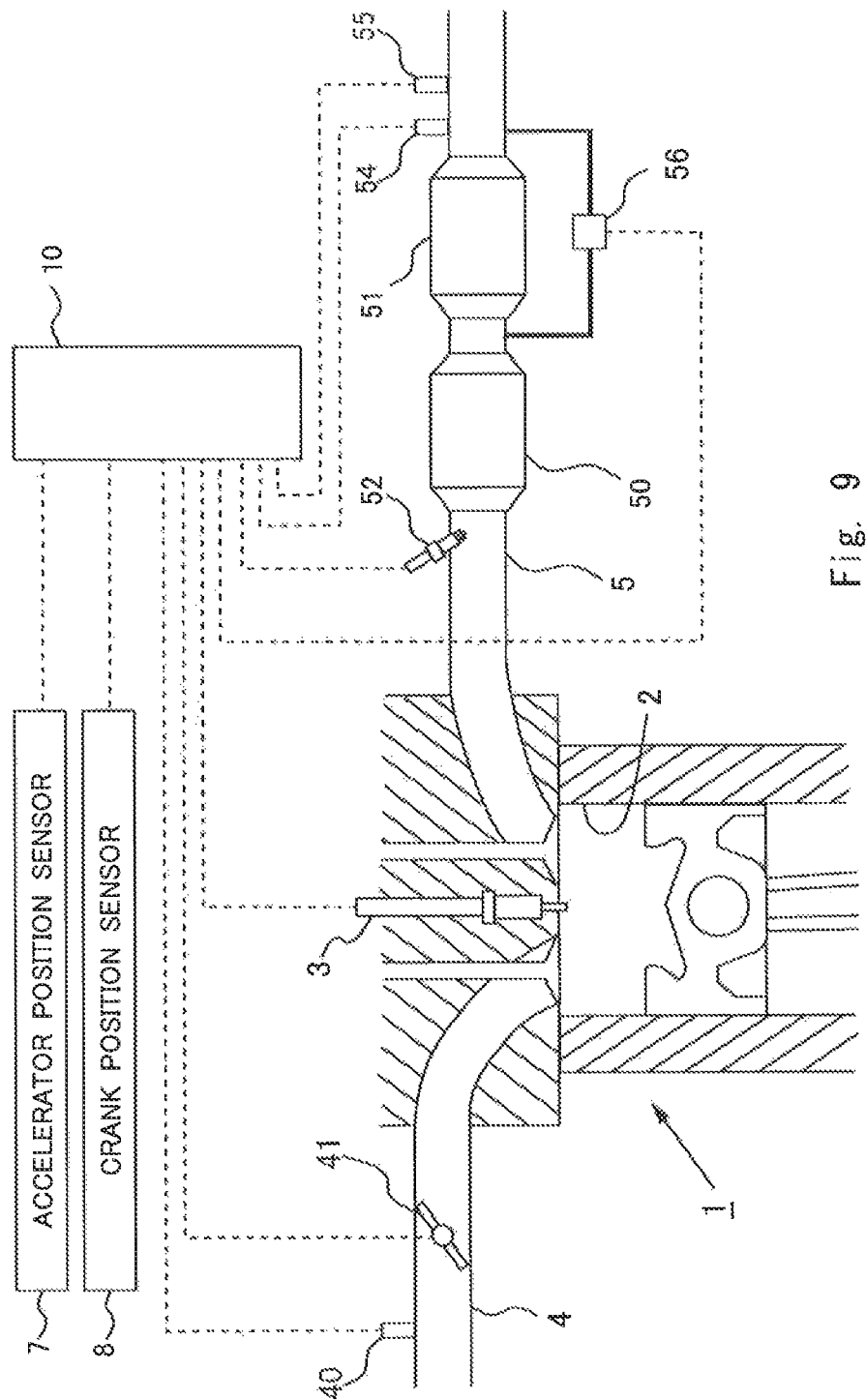
FIG. 9 is a second diagram illustrating the schematic configuration of an internal combustion engine and its intake and exhaust system according to embodiments.

In the configuration of FIG. 9, the state of the filter 51 may be estimated, based on the output value of the differential pressure sensor 56 at the time of completion of the filter recovery process. A deposition amount of PM between the electrodes 551 and 552 of the PM sensor 55 that is estimated on the assumption that the filter 51 is in this estimated state defined as a reference state may be specified as the reference deposition amount of PM. This allows for estimation of the reference deposition amount of PM on the assumption that the state of the filter 51 is close to the actual state to some extent. This provides the higher correlation between the reference deposition amount of PM and the output value of the PM sensor 55 in the case where the output value of the PM sensor 55 is varied by gradually increasing the deposition amount of PM between the electrodes 551 and 552 of the PM sensor 55. As a result, this provides a more noticeable difference between the variation in output value of the PM sensor 55 attributed to the gradual increase of the deposition amount of PM between the electrodes 551 and 552 and the variation in output value of the PM sensor 55 attributed to trapping of extraneous substances between the electrodes 551 and 552. Accordingly, this increases the accuracy of differentiation based on their sensor output change rates as described in the above embodiment.

[Modification 1]

Figure 10:
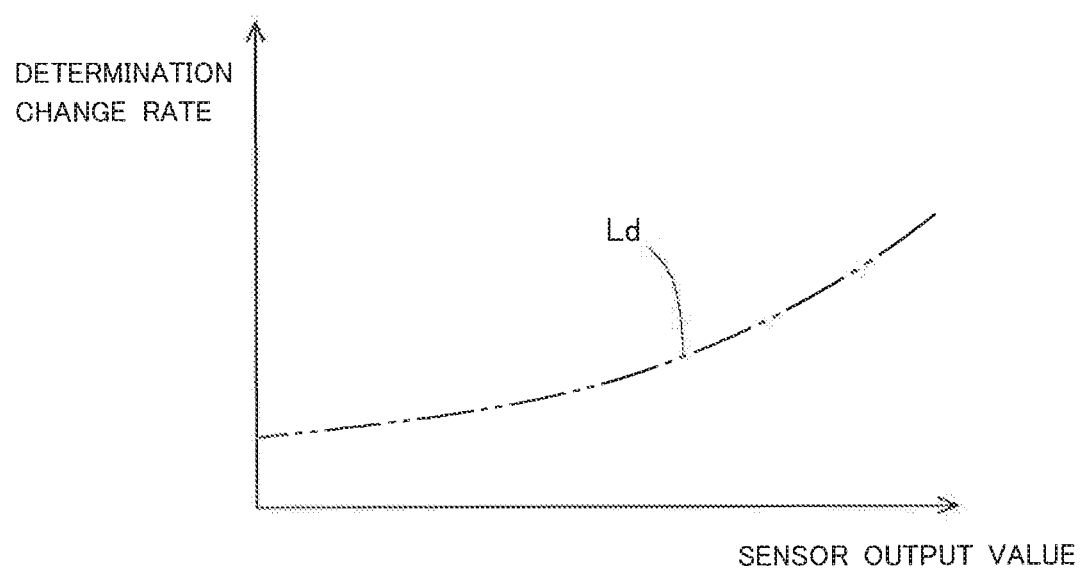
FIG. 10 is a first diagram illustrating a correlation between output value of the PM sensor and determination change rate according to Modification 1 of the embodiment.

The following describes Modification 1 of the above embodiment. This modification changes the determination change rate that is to be compared with the sensor output change rate for determining whether the filter diagnosis process is to be performed or not, according to the output value of the PM sensor 55 at the corresponding time to the sensor output change rate, in place of the reference deposition amount of PM. FIG. 10 is a diagram illustrating a correlation between the output value of the PM sensor 55 and the determination change rate according to this modification. In the graph of FIG. 10, the abscissa shows the output value of the PM sensor 55, and the ordinate shows the determination change rate. In the graph of FIG. 10, a curve Ld shows this correlation. More specifically, the curve Ld in FIG. 10 shows the correlation between the output value of the PM sensor 55 and the determination change rate in the case where the PM sensor 55 is configured to provide an output value corresponding to the value of electric current flowing between the electrodes 551 and 552 and to increase the output value with an increase in deposition amount of PM between the electrodes 551 and 552. In this modification, the determination change rate is set to increase with an increase in output value of the PM sensor 55 as shown by the curve Ld in FIG. 10.

More specifically, the flow of the determination process shown in FIG. 8 uses a map representing the correlation between the output value of the PM sensor 55 and the determination change rate as shown by the curve Ld in FIG. 10 to compute the determination change rate Rth at S204. Unlike the reference deposition amount of PM, however, the output value of the PM sensor 55 is varied by the effect of extraneous substances trapped between the electrodes 551 and 552. Accordingly, at the time when extraneous substances are trapped between the electrodes 551 and 552, the output value of the PM sensor 55 is not correlated with the deposition amount of PM between the electrodes 551 and 552. In this modification, the flow of the determination process shown in FIG. 8 accordingly computes the determination change rate Rth based on the first output value Sout1 out of the first output value Sout1 and the second output value Sout2 that are used for calculation of the sensor output change rate Rsout at S203. In other words, the output value of the PM sensor 55 obtained at S202 in a previous cycle of the flow shown in FIG. 8 is regarded as the output value of the PM sensor 55 at the corresponding time to the sensor output change rate Rsout calculated at S203 in a current cycle. Even when extraneous substances are trapped between the electrodes 551 and 552, this configuration enables the determination change rate Rth to be computed based on the output value of the PM sensor immediately before trapping of the extraneous substances.

Like the above embodiment, setting the determination change rate based on the output value of the PM sensor 55 at the corresponding time to the sensor output change rate according to this modification causes a higher value to be set to the determination change rate in the case where the amount of PM actually depositing between the electrodes 551 and 552 of the PM sensor 55 is expected to be large at the corresponding time to the sensor output change rate, compared with the case where the deposition amount of PM is expected to be small. Like the above embodiment, this modification distinguishes with the higher accuracy whether the change in output value of the PM sensor 55 before elapse of the determination time period dtd since the voltage applying time is to be attributed to the gradual increase in deposition amount of PM between the electrodes 551 and 552 or is to be attributed to trapping of extraneous substances between the electrodes 551 and 552.

Figure 11:
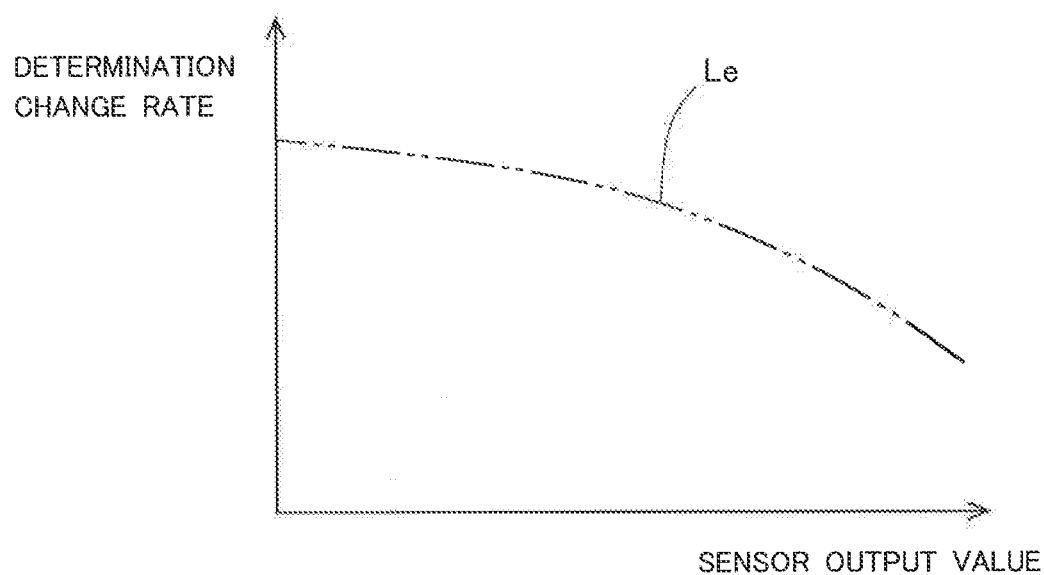
FIG. 11 is a second diagram illustrating a correlation between output value of the PM sensor and determination change rate according to Modification 1 of the embodiment.

In the case where the PM sensor 55 is configured to provide an output value corresponding to the value of resistance between the electrodes 551 and 552 and to decrease the output value with an increase in deposition amount of PM between the electrodes 551 and 552, the correlation between the output value of the PM sensor 55 and the determination change rate is different from the curve Ld shown in FIG. 10. FIG. 11 is a diagram illustrating a correlation between the output value of the PM sensor 55 and the determination change rate in the case where the PM sensor 55 is configured to have such output characteristic. In the graph of FIG. 11, the abscissa shows the output value of the PM sensor 55, and the ordinate shows the determination change rate. In the graph of FIG. 11, a curve Le shows this correlation. As shown by this curve Le in FIG. 11, in the case where the PM sensor 55 is configured to decrease the output value with an increase in deposition amount of PM between the electrodes 551 and 552, the determination change rate is set to increase with a decrease in output value of the PM sensor 55. This causes a higher value to be set to the determination change rate in the case where the amount of PM actually depositing between the electrodes 551 and 552 of the PM sensor 55 is expected to be large at the corresponding time to the sensor output change rate, compared with the case where the deposition amount of PM is expected to be small.

In this modification, the determination change rate may also be set to vary stepwise with an increase or a decrease in output value of the PM sensor 55 at the corresponding time to the sensor output change rate.

[Modification 2]

The following describes Modification 2 of the above embodiment. As described above, the deposition amount of PM between the electrodes 551 and 552 of the PM sensor 55 basically has a gradual increase with time after the voltage applying time. When the abscissa is changed to the time elapsed since the voltage applying time in the upper graph of FIG. 5, the output value of the PM sensor 55 is expected to vary in the same tendency as that shown in FIG. 5. In this modification, the variation in output value of the PM sensor 55 per unit time may thus be specified as the sensor output change rate. In this modification, the sensor output change rate at the time when extraneous substances are trapped between the electrodes 551 and 552 of the PM sensor 55 also becomes higher than the sensor output change rate in the case where the deposition amount of PM between the electrodes 551 and 552 is gradually increased. Accordingly, this sensor output change rate may be used similarly to the variation in output value of the PM sensor 55 per unit increase of the reference deposition amount of PM described above.

Figure 12:
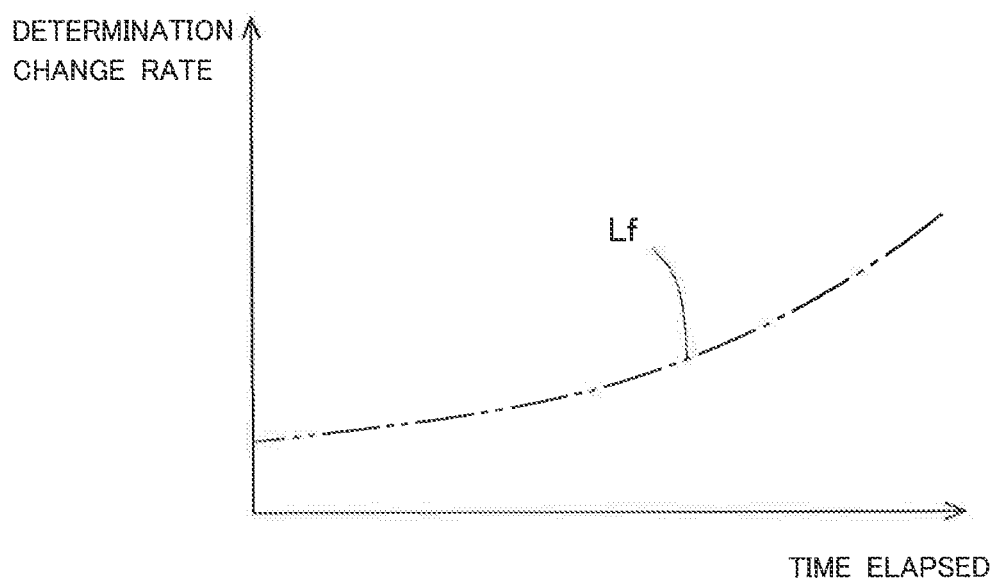
FIG. 12 is a diagram illustrating a correlation between time elapsed since the voltage applying time and determination change rate according to Modification 2 of the embodiment.

This modification changes the determination change rate that is to be compared with the sensor output change rate for determining whether the filter diagnosis process is to be performed or not, according to the time elapsed since the voltage applying time, in place of the reference deposition amount of PM. FIG. 12 is a diagram illustrating a correlation between the output value of the PM sensor 55 and the determination change rate according to this modification. In the graph of FIG. 12, the abscissa shows the time elapsed since the voltage applying time, and the ordinate shows the determination change rate. In the graph of FIG. 12, a curve Lf shows this correlation. In this modification, the determination change rate is set to increase with an increase in time elapsed since the voltage applying time, as shown by the curve Lf in FIG. 12.

Setting the determination change rate based on the time elapsed since the voltage applying time according to this modification causes a higher value to be set to the determination change rate in the case where the amount of PM actually depositing between the electrodes 551 and 552 of the PM sensor 55 is expected to be large at the corresponding time to the sensor output change rate, compared with the case where the deposition amount of PM is expected to be small. Like the above embodiment, this modification distinguishes with the higher accuracy whether the change in output value of the PM sensor 55 before elapse of the determination time period dtd since the voltage applying time is to be attributed to the gradual increase in deposition amount of PM between the electrodes 551 and 552 or is to be attributed to trapping of extraneous substances between the electrodes 551 and 552.

In this modification, the determination change rate may also be set to vary stepwise according to the time elapsed since the voltage applying time.

While the present disclosure has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

REFERENCE SIGNS LIST 1 internal combustion engine
4 intake passage
5 exhaust passage
50 oxidation catalyst
51 particulate filter (filter)
55 PM sensor
550 insulator
551, 552 electrodes
553 sensor element
554 ammeter
555 heater
556 cover
557 through hole
56 differential pressure sensor
60 power source
10 ECU

What is claimed is:

1. An abnormality diagnosis apparatus for a particulate filter that is provided in an exhaust passage of an internal combustion engine to trap particulate matter (PM) included in exhaust gas, the abnormality diagnosis apparatus comprising:
a PM sensor that is provided downstream of the particulate filter in the exhaust passage and is configured to have a pair of electrodes as a sensor element and output a signal corresponding to a deposition amount of PM between the electrodes when electrical continuity is established between the electrodes by deposition of PM between the electrodes, the PM sensor being configured such that a larger deposition amount of PM between the electrodes provides a higher variation in output value of the PM sensor relative to an increase in deposition amount of PM between the electrodes;
a controller comprising at least one processor, the controller being programmed to perform a sensor recovery process of removing PM depositing between the electrodes of the PM sensor, and to perform a filter diagnosis process of diagnosing an abnormality of the particulate filter based on an output value of the PM sensor at a time when a predetermined determination time period has elapsed since a predetermined PM deposition restart time, which is a time when deposition of PM between the electrodes of the PM sensor is restarted after completion of the sensor recovery process; and
a monitor unit that is configured to continuously monitor an output signal of the PM sensor after the PM deposition restart time, wherein
the controller is programmed to determine that the filter diagnosis process is not to be performed when a sensor output change rate becomes higher than a predetermined determination change rate before elapse of the determination time period since the PM deposition restart time, wherein the sensor output change rate is a variation in output value of the PM sensor monitored by the monitor unit per unit increase in reference deposition amount of PM, wherein the reference deposition amount of PM is an estimated value of the deposition amount of PM between the electrodes of the PM sensor on the assumption that the particulate filter is in a predetermined reference state, or a variation in output value of the PM sensor monitored by the monitor unit per unit time; and
the controller is programmed to set a higher value to the determination change rate, which is to be compared with the sensor output change rate, in a case where the deposition amount of PM between the electrodes of the PM sensor is expected to be large at a corresponding time to the sensor output change rate, compared with a case where the deposition amount of PM is expected to be small at the corresponding time to the sensor output change rate.

2. The abnormality diagnosis apparatus for the particulate filter according to claim 1,
wherein the sensor output change rate is the variation in the output value of the PM sensor monitored by the monitor unit per unit increase in the reference deposition amount of PM, and
the controller is programmed to set a higher value to the determination change rate, which is to be compared with the sensor output change rate, in a case where the reference deposition amount of PM is large at the corresponding time to the sensor output change rate, compared with a case where the reference deposition amount of PM is small at the corresponding time to the sensor output change rate.

3. The abnormality diagnosis apparatus for the particulate filter according to claim 1,
wherein the PM sensor is configured to provide an output value corresponding to a value of electric current flowing between the electrodes and to increase the output value with an increase in deposition amount of PM between the electrodes,
the sensor output change rate is the variation in the output value of the PM sensor monitored by the monitor unit per unit increase in the reference deposition amount of PM and is calculated as a ratio of a difference between output values of the PM sensor at two times that are different from each other by a predetermined interval to a difference between reference deposition amounts of PM at the two times, and
the controller is programmed to set a higher value to the determination change rate, which is to be compared with the sensor output change rate, in a case where a first output value that is an output value at an earlier time between the output values of the PM sensor at the two times used to calculate the sensor output change rate is large, compared with a case where the first output value is small.

4. The abnormality diagnosis apparatus for the particulate filter according to claim 1, wherein the PM sensor is configured to provide an output value corresponding to a value of resistance between the electrodes and to decrease the output value with an increase in deposition amount of PM between the electrodes, the sensor output change rate is the variation in the output value of the PM sensor monitored by the monitor unit per unit increase in the reference deposition amount of PM and is calculated as a ratio of a difference between output values of the PM sensor at two times that are different from each other by a predetermined interval to a difference between reference deposition amounts of PM at the two times, and the controller is programmed to set a higher value to the determination change rate, which is to be compared with the sensor output change rate, in a case where a first output value that is an output value at an earlier time between the output values of the PM sensor at the two times used to calculate the sensor output change rate is small, compared with a case where the first output value is large.

5. The abnormality diagnosis apparatus for the particulate filter according to claim 1, wherein the sensor output change rate is the variation in the output value of the PM sensor monitored by the monitor unit per unit time, and the controller is programmed to set a higher value to the determination change rate, which is to be compared with the sensor output change rate, in a case where a long time has elapsed since the PM deposition restart time, compared with a case where a short time has elapsed since the PM deposition restart time.

6. The abnormality diagnosis apparatus for the particulate filter according to claim 1, wherein the sensor output change rate is the variation in the output value of the PM sensor monitored by the monitor unit per unit increase in the reference deposition amount of PM, the abnormality diagnosis apparatus further comprising:

a differential pressure sensor that is configured to output a signal corresponding to a difference in exhaust pressure between upstream and downstream of the particulate filter, wherein the controller is programmed to further perform a filter recovery process, the filter recovery process being a process of removing PM depositing on the particulate filter; and a state of the particulate filter is estimated based on an output value of the differential pressure sensor at a time when the filter recovery process performed by the controller is completed prior to execution of the sensor recovery process by the controller, and the reference deposition amount of PM is estimated on the assumption that the particulate filter is in the estimated state specified as the reference state.

\* \* \* \* \*